(12) United States Patent
Cahill

(10) Patent No.: US 10,874,442 B2
(45) Date of Patent: Dec. 29, 2020

(54) MULTI-MODE TORQUE DRIVERS EMPLOYING INNER SURFACES COMPATIBLE WITH PEDICLE SCREW GUIDE WIRES, AND RELATED SYSTEMS AND METHODS

(71) Applicant: Kevin S. Cahill, Wrightsville Beach, NC (US)

(72) Inventor: Kevin S. Cahill, Wrightsville Beach, NC (US)

(73) Assignee: Power T Handle, LLC, Supply, NC (US)

( * ) Notice: Subject to any disclaimer, the term of this patent is extended or adjusted under 35 U.S.C. 154(b) by 158 days.

(21) Appl. No.: 16/224,784

(22) Filed: Dec. 18, 2018

(65) Prior Publication Data

US 2019/0223923 A1    Jul. 25, 2019

Related U.S. Application Data

(63) Continuation-in-part of application No. 14/757,804, filed on Dec. 23, 2015, now Pat. No. 10,349,984.

(51) Int. Cl.
*A61B 17/70* (2006.01)
*A61B 17/86* (2006.01)
(Continued)

(52) U.S. Cl.
CPC ...... *A61B 17/7082* (2013.01); *A61B 17/7071* (2013.01); *A61B 17/848* (2013.01);
(Continued)

(58) Field of Classification Search
CPC . A61B 17/70; A61B 17/7082; A61B 17/7071; A61B 17/84; A61B 17/848; A61B 17/846; A61B 17/86; A61B 17/864
See application file for complete search history.

(56) References Cited

U.S. PATENT DOCUMENTS

D113,158 S    1/1939  Cashmore
3,802,518 A   4/1974  Albert
(Continued)

OTHER PUBLICATIONS

International Search Report and Written Opinion, PCT/US2016/068150, dated May 4, 2017.
(Continued)

*Primary Examiner* — Christopher J Beccia
(74) *Attorney, Agent, or Firm* — Stephen R. Bylciw, Esq.

(57) ABSTRACT

Multi-mode torque drivers employing inner surfaces compatible with pedicle screw guide wires, and related systems and methods are disclosed. A spinal column includes vertebrae in an articulating structure protecting a spinal cord. Medical intervention may involve limiting the relative motion between vertebrae by fusing vertebrae together with mechanical assemblies, including pedicle screws attached to the vertebrae. A multi-mode torque driver may be used to form the pedicle screw attachments with vertebrae. By including a passageway for a guide wire along an output rotational axis of a pedicle screw torque driver, pedicle screws may be inserted into a vertebra along a desired trajectory previously defined using the guide wire. In this manner, pedicle screws may be inserted into vertebrae precisely and efficiently.

19 Claims, 14 Drawing Sheets

(51) Int. Cl.
  *A61B 17/84* (2006.01)
  *B25B 21/00* (2006.01)
  *B25B 15/02* (2006.01)
  *A61B 17/88* (2006.01)
  *A61B 17/00* (2006.01)

(52) U.S. Cl.
  CPC ........ *A61B 17/864* (2013.01); *A61B 17/8875* (2013.01); *B25B 15/02* (2013.01); *B25B 21/00* (2013.01); *A61B 2017/00398* (2013.01); *A61B 2017/00407* (2013.01)

(56) References Cited

U.S. PATENT DOCUMENTS

| | | |
|---|---|---|
| 4,078,589 A | 3/1978 | Miller |
| D287,814 S | 1/1987 | Hiraishi et al. |
| 4,754,669 A | 7/1988 | Verdier |
| 5,016,501 A | 5/1991 | Holzer |
| D339,279 S | 9/1993 | Baum |
| D392,535 S | 3/1998 | Vasudeva et al. |
| 5,788,021 A * | 8/1998 | Tsai ................. B25B 21/00 188/67 |
| D409,463 S | 5/1999 | McMullin |
| 6,151,998 A | 11/2000 | Fu-Hui |
| 6,220,368 B1 | 4/2001 | Ark et al. |
| 6,273,200 B1 | 8/2001 | Smith et al. |
| 7,048,107 B1 | 5/2006 | Geis et al. |
| D557,584 S | 12/2007 | Gao |
| D613,144 S | 4/2010 | Lin |
| D646,385 S | 10/2011 | Gauthier et al. |
| 8,104,145 B1 | 1/2012 | Hajianpour |
| D654,589 S | 2/2012 | Bast et al. |
| D673,832 S | 1/2013 | Molina et al. |
| 8,601,916 B2 | 12/2013 | Chen |
| 8,651,198 B2 | 2/2014 | Ito |
| D734,115 S | 7/2015 | Robinson et al. |
| D784,105 S | 4/2017 | Nelson |
| 2005/0033292 A1 * | 2/2005 | Teitelbaum ........ A61B 17/1617 606/53 |
| 2007/0132196 A1 | 6/2007 | Puzio et al. |
| 2009/0254094 A1 | 10/2009 | Knapp et al. |
| 2009/0299439 A1 | 12/2009 | Mire et al. |
| 2010/0179560 A1 | 7/2010 | Chenaux |
| 2012/0046665 A1 * | 2/2012 | Kim .................... A61B 17/7082 606/104 |
| 2012/0109143 A1 | 5/2012 | Steele et al. |

OTHER PUBLICATIONS

"Black and Decker Gyro Screwdriver—M3 Design Product Teardown," M3 Design, (downloaded from internet at: cdn1.m3design.com/wordpress/wp-content/uploads/2014/09/M3-Teardown-Black-Decker-Gyro-Screwdriver.pdf), dated Sep. 2014.

* cited by examiner

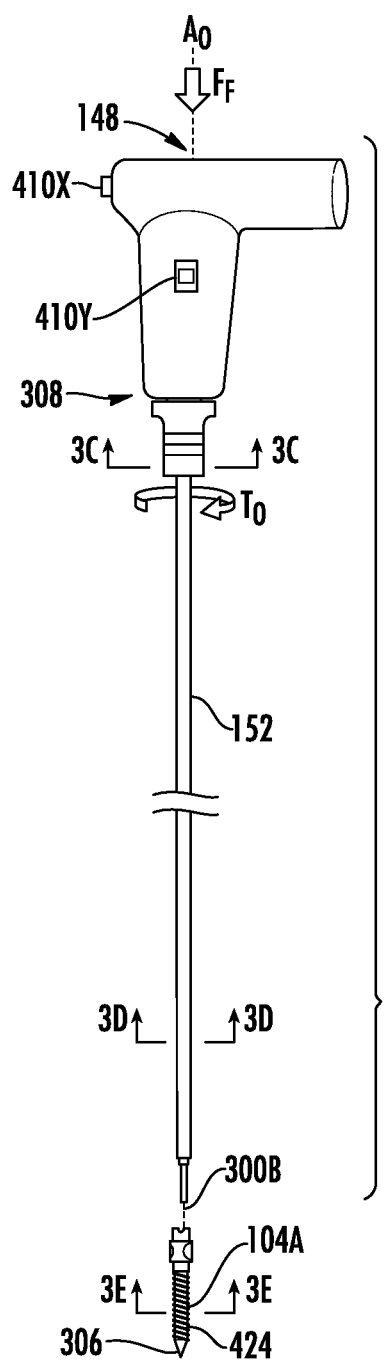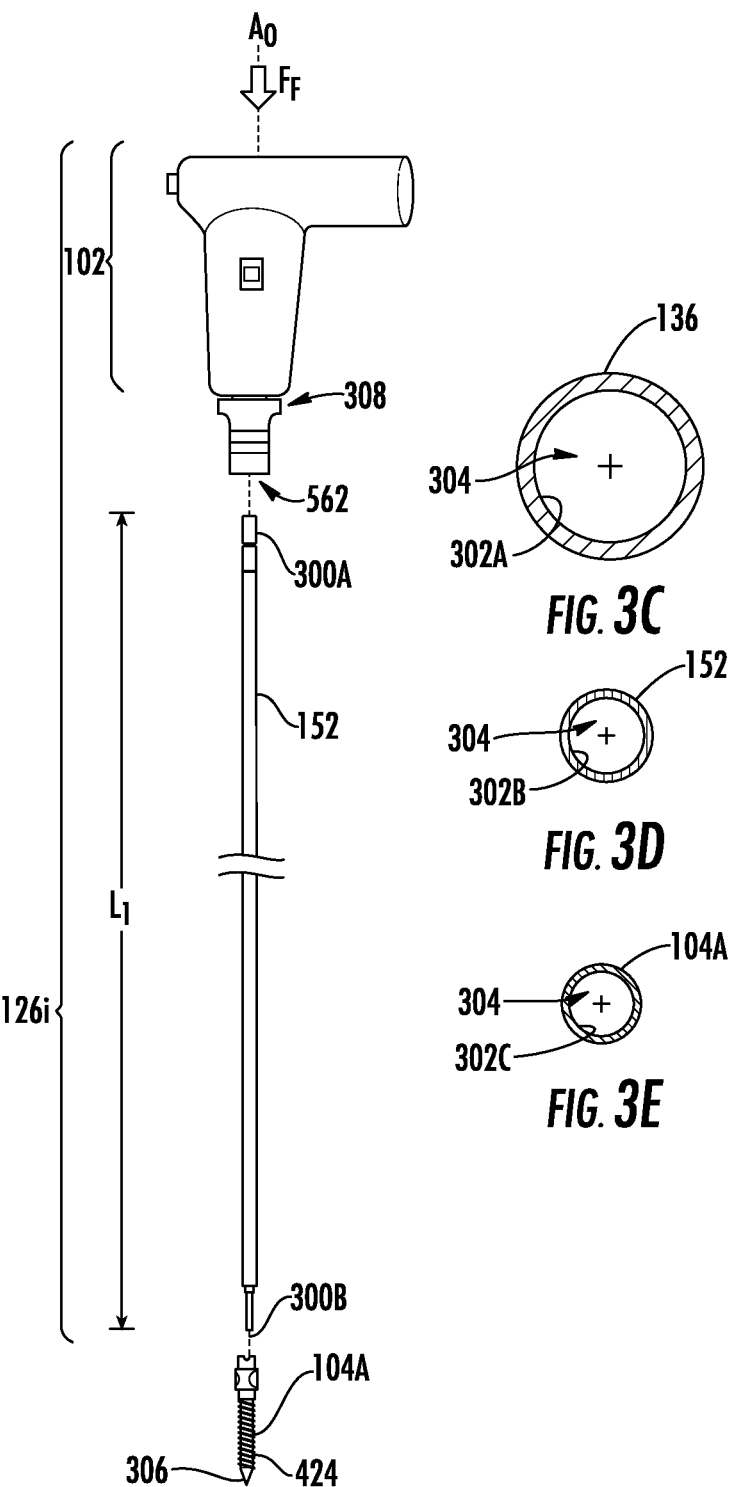
FIG. 3A
FIG. 3B
FIG. 3C
FIG. 3D
FIG. 3E

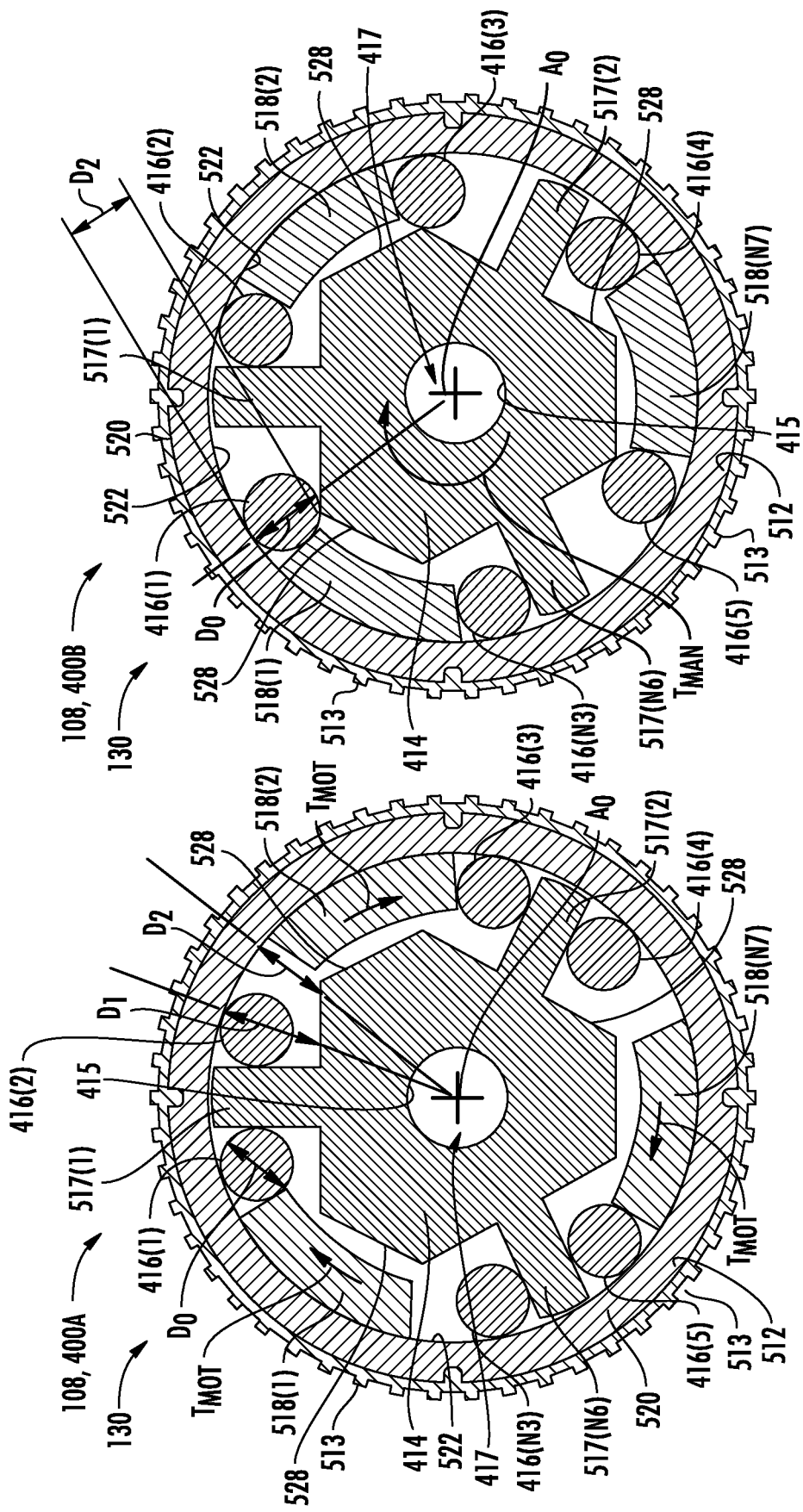

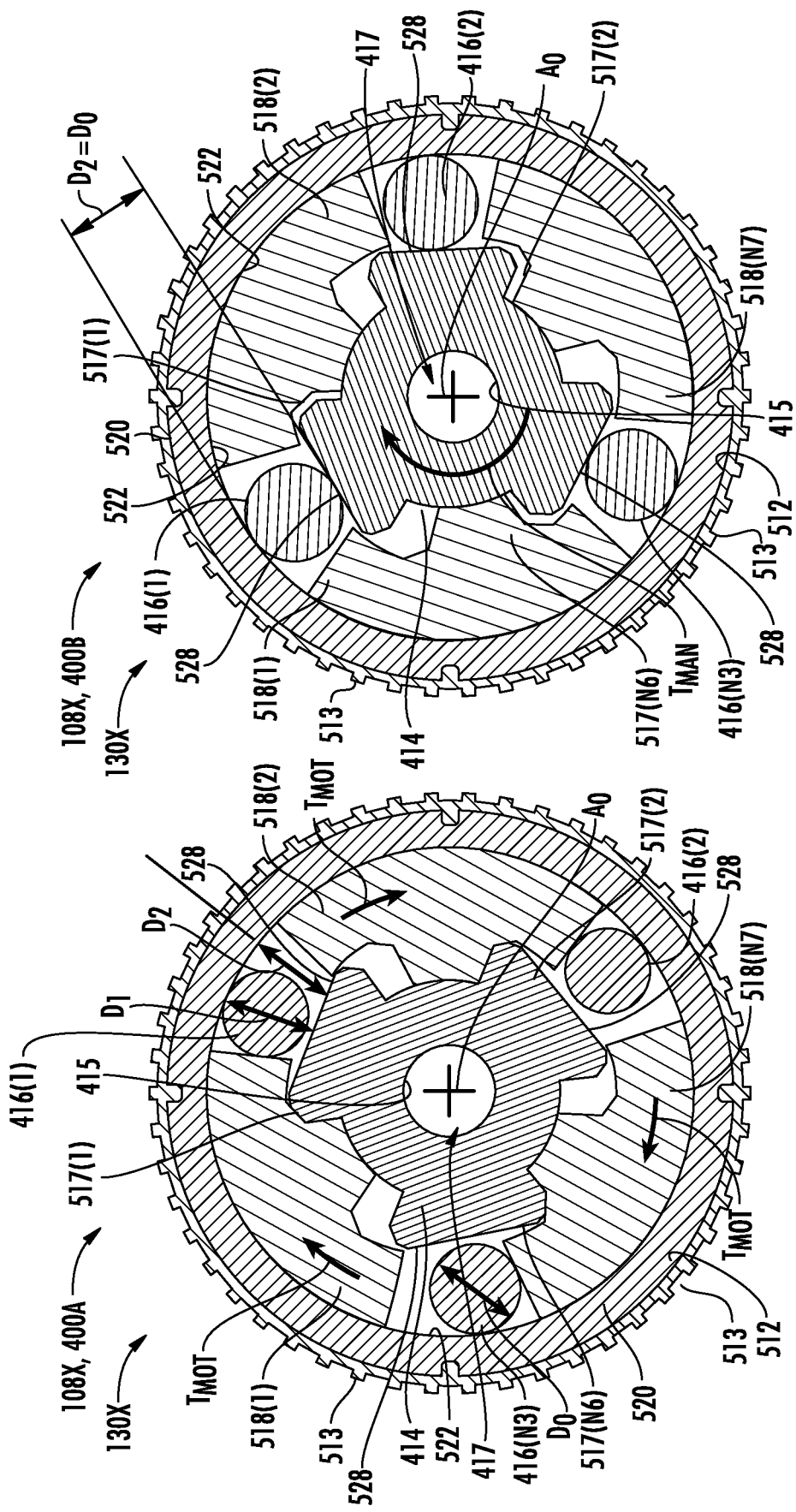

MULTI-MODE TORQUE DRIVERS EMPLOYING INNER SURFACES COMPATIBLE WITH PEDICLE SCREW GUIDE WIRES, AND RELATED SYSTEMS AND METHODS

CROSS-REFERENCE TO RELATED APPLICATION

This application is a continuation-in-part of co-pending U.S. patent application Ser. No. 14/757,804, filed Dec. 23, 2015 and titled "MULTI-MODE TORQUE DRIVERS EMPLOYING ANTI-BACKDRIVE UNITS FOR MANAGING PEDICLE SCREW ATTACHMENTS WITH VERTEBRAE, AND RELATED SYSTEMS AND METHODS."

BACKGROUND

Field of the Disclosure

The technology of the disclosure relates to surgical screwdriver devices and related assemblies and methods for creating and removing pedicle screw attachments with vertebrae.

Technical Background

A vertebral column and a spinal cord of a patient extend from the skull to the pelvis and form a longitudinal axis of a patient. The column includes vertebra that are separated by fibrocartilage structures (intervertebral disks) that are interconnected with ligaments. The cord is disposed within a vertebral canal formed by openings in each of the vertebrae enabling the vertebrae collectively, as part of the column, to enclose the cord and thereby provide protection. The spinal cord along with nerves extending from the spinal cord form a central nervous system enabling communication between the brain and other parts of the patient. The nerves exit the vertebral canal through passageways between adjacent vertebrae and form connections with the other patient parts.

The vertebral column typically facilitates movement of the patient by enabling relative movement between adjacent vertebrae and often serves its functions without issues, but abnormalities may occur necessitating medical intervention. In one example, one or more portions of the vertebral column may have abnormalities from development issues and/or trauma making relative movement at these locations problematic as injury or discomfort may occur to the spinal cord or the other nerves. Medical intervention may be necessary to stop relative movement at these locations. Types of exemplary abnormalities include degenerative disc disease, spondylolisthesis, trauma, deformities, tumors, stenosis, and pseudoarthrosis (earlier failed spine surgery). Pain may be lessened and/or opportunities for healing may occur once relative movement is prevented.

Conventional spine fusion is one surgical approach for permanently or temporarily immobilizing adjacent vertebrae relative to each other. In this approach, fasteners (e.g., pedicle screws) are attached to the adjacent vertebrae to serve as anchor points, and these anchor points are interconnected with at least one immobilizing rod to stop relative movement between the adjacent vertebrae. Conventionally an attending surgeon typically attaches the pedicle screws and a connecting rod to adjacent vertebrae by screwing these pedicle screws into the adjacent vertebrae with a surgical screwdriver. The desired trajectory of each screw into the desired vertebra is carefully selected to avoid damage to the spinal cord and nerve fibers extending therefrom between vertebrae. The desired trajectory is also selected to achieve a stable and strong attachment between the screw and the vertebrae. The advantage to achieving a strong pedicle screw attachment to the vertebra is that the adjacent vertebrae are immobilized with respect to each other when the interconnection rod is connected to the pedicle screws.

Inserting and retracting the pedicle screw into and from the vertebrae is difficult, because it is a physically demanding task for the surgeon and requires precision to avoid inflicting nerve injuries to the patient. Specifically, surgeons have traditionally utilized manual screwdrivers to ensure that the screws are inserted precisely along the desired trajectory and that the final position of the screw results in a strong attachment. The proximity of the desired trajectory of the pedicle screw to the spinal cord and spinal nerves makes it imperative to precisely follow the desired trajectory and the manual screwdrivers can provide the precision and heightened feedback desired by the surgeon.

The manual screwdriver also requires the surgeon to manually apply a relatively high torque, which when applied, can be easily monitored by the surgeon to understand whether a strong pedicle screw attachment has been achieved. However, manually applying a high torque to gain precision is gained at the expense of repetitive motion injuries (e.g., lateral epicondylitis) suffered by many attending surgeons. Accordingly, what is needed is a medical device to precisely insert pedicle screws as part of pedicle screw attachments without injury to patients and surgeons.

SUMMARY OF THE DETAILED DESCRIPTION

Embodiments disclosed herein include multi-mode torque drivers employing inner surfaces compatible with pedicle screw guide wires, and related systems and methods. A spinal column includes vertebrae in an articulating structure protecting a spinal cord. Medical intervention may involve limiting the relative motion between vertebrae by fusing vertebrae together with mechanical assemblies, including pedicle screws attached to the vertebrae. A multi-mode torque driver may be used to form the pedicle screw attachments with vertebrae. By including a passageway for a guide wire along an output rotational axis of a pedicle screw torque driver, pedicle screws may be inserted into a vertebra along a desired trajectory previously defined using the guide wire. In this manner, pedicle screws may be inserted into vertebrae precisely and efficiently.

In one embodiment, a main body of a multi-mode torque driver for managing a pedicle screw attachment with a vertebra is disclosed. The main body includes a center portion extending along an output rotational axis from a first end to a second end, wherein the center portion is arranged to transfer a manual torque from the first end to the second end. The main body further includes an inner surface forming an inner space and the inner surface connecting a cannulation port at the first end to an output opening at the second end, wherein the inner space includes a motor interface configured to receive a motor coupled to the inner surface, wherein the output opening is configured for an output element to extend through the output opening and convey a motorized torque from the motor during a power mode and the manual torque during a manual mode. The output rotational axis extends through both the cannulation port and the output opening. In this manner, the user can efficiently provide motorized torque in a power mode, and precisely provide manual torque and valuable levels of tactile feedback in the manual mode.

In another embodiment, a multi-mode torque driver for managing a pedicle screw attachment with a vertebra is disclosed. The multi-mode torque driver includes a main body extending along an output rotational axis from a first end to a second end, the main body including an inner surface forming an inner space connecting a cannulation port at the first end to an output opening at the second end. The multi-mode torque driver also includes a motor assembly disposed within the inner space. The multi-mode torque driver further includes a motor disposed within the inner space. The multi-mode torque driver further includes an anti-backdrive unit coupled to the motor assembly, the anti-backdrive unit including an output element disposed at the output opening and along the output rotational axis. The output element and the main body are configured to receive a guide wire element along the output rotational axis and through the output passageway and cannulation port while managing the pedicle screw attachment. In this manner, spinal surgeries can be completed in a shorter time while ensuring that pedicle screw attachments are created that are strong and stable over time while avoiding injury to the patient and surgeon.

In another embodiment, a method is disclosed for managing a pedicle screw attachment with a vertebra. This method may include receiving a guide wire with the multi-mode torque driver, wherein the guide wire is received along the output rotational axis and through the output passageway and the cannulation port. The method may further include transmitting, with the output element of an anti-backdrive unit disposed within a main body of a multi-mode torque driver, the system torque from the output element to the pedicle screw, wherein the system torque includes a manual torque during a manual mode and a motorized torque during a power mode, wherein the system torque moves the pedicle screw relative to the vertebra. The method may further include generating, with a motor assembly disposed within the main body, the motorized torque during the power mode and transmitting the motorized torque to the anti-backdrive unit with the motor assembly in the power mode. The method may further include upon applying the manual torque to the main body with a single hand of a user while the output element is coupled to the pedicle screw and the output element is free from the motorized torque, automatically locking the output element in the manual mode relative to the main body and transmitting the manual torque from the main body to the output element in the manual mode. In this manner, immobilization systems including pedicle screw attachments are formed more efficiently to minimize surgical times that when occurring with shorter durations may reduce infection rates or other complications for patients.

Additional features and advantages will be set forth in the detailed description which follows, and in part will be readily apparent to those skilled in the art from that description or recognized by practicing the embodiments as described herein, including the detailed description that follows, the claims, as well as the appended drawings.

It is to be understood that both the foregoing general description and the following detailed description present embodiments, and are intended to provide an overview or framework for understanding the nature and character of the disclosure. The accompanying drawings are included to provide a further understanding, and are incorporated into and constitute a part of this specification. The drawings illustrate various embodiments, and together with the description serve to explain the principles and operation of the concepts disclosed.

BRIEF DESCRIPTION OF THE FIGURES

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, may admit to other equally effective embodiments.

FIGS. 3A and 3B are a front view and a partially disassembled front view, respectively, of the exemplary pedicle screw system of FIG. 1D aligned along an output rotational axis with the pedicle screw;

FIGS. 3C through 3E are respective sectional views of an adapter chuck of the multi-mode torque driver, a screw interface of the pedicle screw system, and the pedicle screw of FIG. 3A;

FIGS. 4D-1 and 4D-2 are exemplary graphs of system torque produced by the multi-mode torque driver of FIG. 4A and resistance torque provided to the multi-mode torque driver, respectively, over an exemplary time period during the power and manual modes illustrating the resistance torque greater than a resistance threshold;

FIGS. 4E-1 and 4E-2 are exemplary graphs of system torque produced by the multi-mode torque driver of FIG. 4A and resistance torque provided to the multi-mode torque driver, respectively, over an exemplary second time period during the power and manual modes illustrating the resistance torque temporarily less than the resistance threshold;

FIGS. 6A and 6B are partial top sectional views parallel to the output rotational axis of the multi-mode torque driver in FIGS. 4A and 4B, respectively, illustrating the anti-backdrive unit operating in the power and manual modes;

FIGS. 8A and 8B are partial top sectional views parallel to the output rotational axis of a second embodiment of a multi-mode torque driver illustrating another embodiment of an anti-backdrive unit operating in power and manual modes, respectively.

To facilitate understanding, identical reference numerals have been used, where possible, to designate identical elements that are common to the figures. It is contemplated that elements and features of one embodiment may be beneficially incorporated in other embodiments without further recitation.

DETAILED DESCRIPTION

Reference will now be made in detail to the embodiments, examples of which are illustrated in the accompanying drawings, in which some, but not all embodiments are shown. Indeed, the concepts may be embodied in many different forms and should not be construed as limiting herein; rather, these embodiments are provided so that this disclosure will satisfy applicable legal requirements. Whenever possible, like reference numbers will be used to refer to like components or parts.

Embodiments disclosed herein include multi-mode torque drivers employing inner surfaces compatible with pedicle screw guide wires, and related systems and methods. A spinal column includes vertebrae in an articulating structure protecting a spinal cord. Medical intervention may involve limiting the relative motion between vertebrae by fusing vertebrae together with mechanical assemblies, including pedicle screws attached to the vertebrae. A multi-mode torque driver may be used to form the pedicle screw attachments with vertebrae. By including a passageway for a guide wire along an output rotational axis of a pedicle screw torque driver, pedicle screws may be inserted into a vertebra along a desired trajectory previously defined using the guide wire. In this manner, pedicle screws may be inserted into vertebrae precisely and efficiently.

Figure 1A:
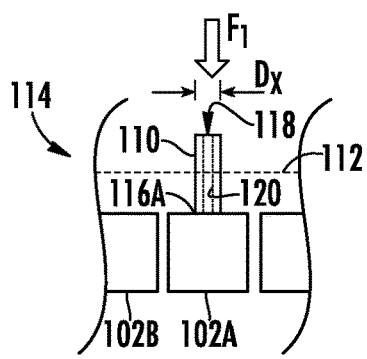
FIG. 1A is a schematic of an exemplary large bore needle accessing an exemplary pedicle of a vertebra under skin of a patient as is known in the art.

In this regard, FIGS. 1A through 1I are schematic representations of an exemplary process to install an exemplary immobilization system 100 (FIG. 1I) to fuse adjacent vertebrae 102A, 102B together. The immobilization system 100 may include a pedicle screw 104A guided (or positioned) by a guide wire 106 relative to the vertebrae 102A, 102B and inserted into the vertebra 102A with a multi-mode torque driver 108 of a pedicle screw system 126. To begin, FIG. 1A is a schematic of an exemplary large bore needle 110 (e.g. Jamshidi™ needle) accessing an exemplary pedicle 116A of the vertebra 102A by being inserted through skin 112 of a patient 114 as is known in the art. The large bore needle 110 may, for example, have an outer diameter DX of 3.5 millimeters. A surgeon or user 125 may guide the large bore needle 110 to an intersection of the facet and the transverse process of the vertebra 102A using anterior-posterior and lateral imaging (e.g. fluoroscopy) and then may be further inserted at least partially through the pedicle 116A using an impact device (e.g. slap hammer) applying a force F1 to the large bore needle 110. The large bore needle 110 includes a passageway 118 formed by an inner surface 120 of the large bore needle 110. This passageway 118 may be disposed along the later trajectory of the pedicle screw 104A through the pedicle 116A. In this manner, the passageway 118 of the large bore needle 110 may enable initial access to the pedicle 116A of the vertebra 102A.

Figure 1B:
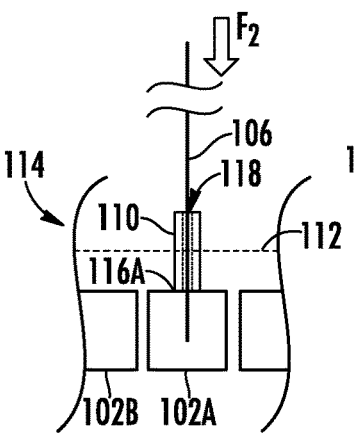
FIG. 1B is a schematic of an exemplary guide wire being inserted into the pedicle of FIG. 1A though the large bore needle as is known in the art.

Next, the guide wire 106 may be precisely positioned to set the desired trajectory of the pedicle screw 104A to anchor the immobilization system 100 in order to fuse the vertebrae 102A, 102B together. FIG. 1B is a schematic of an exemplary guide wire 106 (e.g. Kirschner wire) being inserted into the pedicle 116A of FIG. 1A though the passageway 118 of the large bore needle 110 as is known in the art. The guide wire 106 may have a diameter, for example, in a range from 1.3 millimeters to 2.0 millimeters and may be inserted into the pedicle with a force F2 applied by a force application tool (not shown), for example, slap hammer. In this manner, the guide wire 106 may be positioned to define a trajectory for the later insertion of the pedicle screw into the vertebra 102A.

Figure 1C:
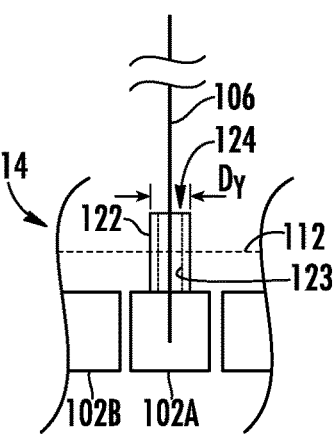
FIG. 1C is a schematic of an exemplary tissue spreader replacing the large bore needle of FIG. 1B as is known in the art.

Once the guide wire 106 is positioned a larger passageway may be created through the skin 112 and tissue to accommodate the pedicle screw 104A and the pedicle screw system 126. FIG. 1C is a schematic of an exemplary tissue spreader 122 or tap sleeve replacing the large bore needle 110 of FIG. 1B as is known in the art. The tissue spreader 122 may have an outer diameter DY larger than the outer diameter DX of the large bore needle 110 to prevent tissues of the patient 114 from contacting the threads of the pedicle screw 104A during insertion. The tissue spreader 122 may include an inner surface 123 forming a passageway 124 through the tissue spreader 122. The passageway 124 may be used to surround the guide wire 106 and facilitate the insertion of the pedicle screw 104A threaded through the guide wire 106 to be inserted into the pedicle 116A of the vertebra 102A. In one embodiment, the tissue spreader 122 may be inserted around the large bore needle 110 and through the skin 112 of the patient 114 to the vertebra 102A. Then, the large bore needle 110 may be removed from the patient 114 leaving the guide wire 106 surrounded by the tissue spreader 122. In this manner, the passageway 124 is prepared to receive the pedicle screw 104A.

Figure 1D:
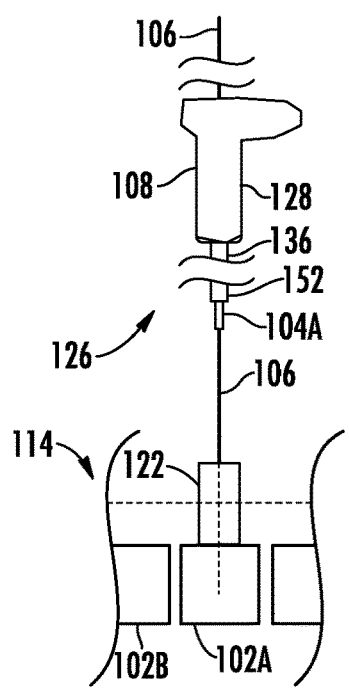
FIG. 1D is a schematic view of a guide wire threaded through an exemplary multi-mode torque driver of a pedicle screw system, and through a pedicle screw coupled to the multi-mode torque driver of FIG. 1C.

The pedicle screw system 126 may now be readied to insert the pedicle screw into the vertebra 102A. FIG. 1D is a schematic of an exemplary multi-mode torque driver 108 of a pedicle screw system 126 coupled to a cannulated pedicle screw 104A and both the multi-mode torque driver 108 and the pedicle screw 104A being threaded onto the guide wire 106 of FIG. 1C. The threading of the guide wire 106 through the pedicle screw 104A and multi-mode torque driver 108 may be better understood with an introduction to the multi-mode torque driver 108 as illustrated in FIG. 2.

Figure 2:
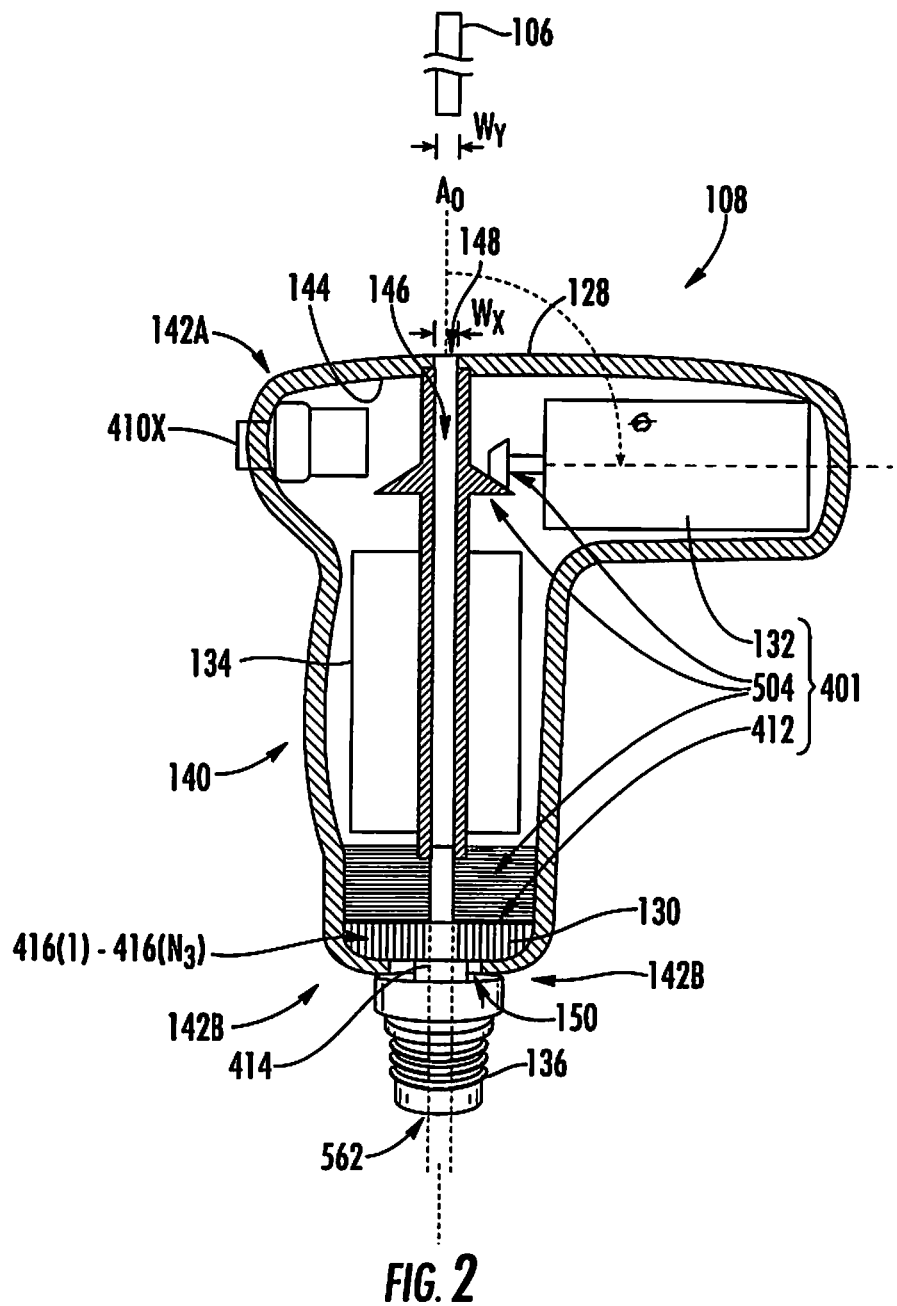
FIG. 2 is a front sectional schematic view of the multi-mode torque driver of the pedicle screw system of FIG. 1D proximate to a guide wire.

FIG. 2 is a front sectional schematic view of the multi-mode torque driver 108 of the pedicle screw system 126 of FIG. 1D proximate to a guide wire 106. The multi-mode torque driver 108 may include a main body 128, an anti-backdrive unit 130, motor 132 of a motor assembly 401, battery 134, and an adapter chuck 136. The main body 128 provides a user interface and an enclosure for the anti-backdrive unit 130, the motor 132, and the battery 134. The anti-backdrive unit 130 enables a power mode 400A and a manual mode 400B to insert the pedicle screw 104A having a longitudinal screw axis A4 into the vertebra 102A as discussed in more detail later. The motor 132 provides a motor torque $T_{MOT}$ for the multi-mode torque driver 108 in the power mode 400A using power from the battery 134. The motor 132 may deliver rotational energy at a transmission angle θ (theta) relative to the output rotational axis A0 of the multi-mode torque driver 108. The adapter chuck 136 enables a standard interface to enable coupling to the pedicle screw 104A via a screw interface 152 (FIG. 3A). These are components of the multi-mode torque driver 108.

Threading of the guide wire 106 may be facilitated by the main body 128. The main body 128 includes a center portion 140 extending along an output rotational axis A0 from a first end 142A to a second end 142B. The main body 128 may further include an inner surface 144 forming an inner space 146 and the inner surface 144 may connect a cannulation port 148 at the first end 142A to an output opening 150 at the second end 142B. The inner surface 144 may facilitate threading of the guide wire 106 between the cannulation port 148 and the output opening 150 along the output rotational axis A0 of the multi-mode torque driver 108. The guide wire 106 may first be inserted through (or threaded through) the adapter chuck 136 and then through the main body 128 from the output opening 150 to the cannulation port 148. The cannulation port 148 may, for example, have a width WX in a range from two (2) millimeters to three (3) millimeters to accommodate the guide wire 106 having a width WY in a range from 1.3 millimeters to two (2) millimeters. In this manner, the guide wire 106 may be threaded through the multi-mode torque driver 108.

Now that the multi-mode torque driver 108 has been briefly introduced, details of the pedicle screw system 126 are now provided. FIGS. 3A and 3B are a front view and a partially disassembled front view, respectively, of the exemplary pedicle screw system 126 of FIG. 1D aligned with the pedicle screw 104A along the output rotational axis A0. The pedicle screw system 126 includes the multi-mode torque driver 108, and the screw interface 152. Different types of the pedicle screw 104A may be used according to the type of the immobilization system 100 (FIG. 1I) being created. Some of the pedicle screws 104A present different interfaces for the pedicle screw system 126, so the screw interface 152 may be selected compatible with the pedicle screw 104A and utilized as part of the pedicle screw system 126. The screw interface 152 extends longitudinally along the output rotational axis A0 and a length L1 from a standard connection end 300A to a screw coupling end 300B. The screw coupling end 300B is configured to couple with the pedicle screw 104A and the standard connection end 300A is designed to couple with the adapter chuck 136, so that a system torque T0 may be transmitted between the multi-mode torque driver 108 and the screw interface 152 in at least one of a clockwise or counter-clockwise direction. In this manner, the multi-mode torque driver 108 may be used with different types of pedicle screws 104A by using different versions of the screw interface 152.

With continued reference to FIGS. 3A and 3B, the standard connection end 300A may have a standard coupling configuration (e.g., quarter inch square), so that the screw interface 152 may be compatible with coupling to various torque drivers, including the multi-mode torque driver 108. The screw interface 152 includes the length L1 which may be selected to allow the multi-mode torque driver 108 to be disposed the length L1 away from the vertebra 102A during surgery to permit the user 125 or surgeon to most conveniently perform other non-insertion tasks (e.g., wound drainage) around the vertebrae 102A without having the multi-mode torque driver 108 becoming an obstruction.

FIGS. 3C through 3E are respective sectional views of the adapter chuck 136, the screw interface 152, and the pedicle screw 104A. Inner surfaces 302A, 302B, 302C respectively of the adapter chuck 136, screw interface 152, and the pedicle screw 104A form a passageway 304 for the guide wire 106 from a leading tip 306 of the pedicle screw 104A to the driven side 308 of the adapter chuck 136 when the pedicle screw 104A is coupled to the screw interface 152. Also, the driven side 308 of the adapter chuck 136 may be coupled to an output element 414 of the anti-backdrive unit 130. The output element 414 may include an inner surface 415 forming a passageway 417 (FIG. 5H) from the coupling opening 562 (FIG. 2) of the adapter chuck 136 and through the output opening 150 of the multi-mode torque driver 108. As discussed in relation to FIG. 2, the inner space 146 of the multi-mode torque driver 108 may form a passageway for the guide wire 106 from the output opening 150 to the cannulation port 148. Accordingly, the guide wire 106 may be threaded through the pedicle screw 104A, screw interface 152, adapter chuck 136, and multi-mode torque driver 108 via the passageways 304, 417 and the inner space 146. In this manner, the guide wire 106 may be threaded through the pedicle screw 104A and the pedicle screw system 126.

Figure 1E:
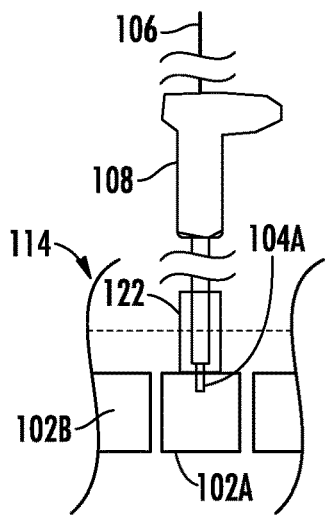
FIGS. 1E and 1F are schematic views of the pedicle screw of FIG. 1D being inserted into the vertebra using motorized and manual modes respectively of the multi-mode torque driver.
Figure 1F:
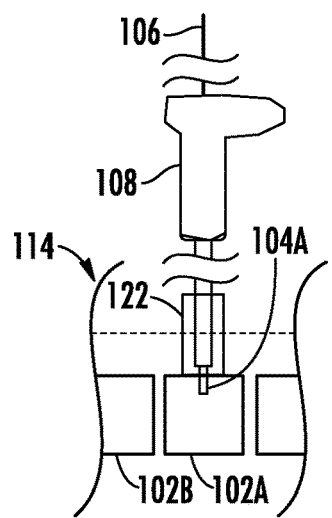
Figure 1G:
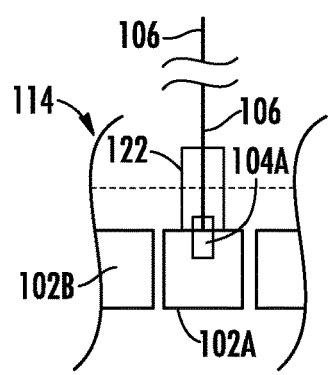
FIG. 1G is a schematic view of the pedicle screw of FIG. 1F attached to the vertebra while the guide wire is unthreaded from the multi-mode torque driver.
Figure 1H:
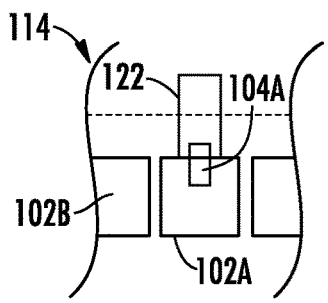
FIG. 1H is a schematic of the pedicle screw of FIG. 1G attached to the vertebra, wherein the guide wire is removed from the vertebra as is known in the art.
Figure 1I:
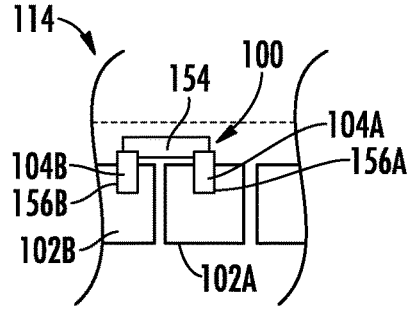
FIG. 1I is a schematic of the tissue spreader of FIG. 1H removed, while a second pedicle screw has been coupled to the pedicle screw of FIG. 1H via a connecting rod as is known in the art.

With the pedicle screw system 126 threaded on the guide wire 106, FIGS. 1E and 1F are schematic views of the pedicle screw 104A of FIG. 1D being inserted into the vertebra 102A using motorized and manual modes respectively of the multi-mode torque driver 108. FIG. 1G is a schematic view of the cannulated pedicle screw of FIG. 1F attached to the vertebra 102A with a pedicle screw attachment 156A while the multi-mode torque driver 108 is unthreaded from the guide wire 106. FIG. 1H is a schematic of the pedicle screw 104A of FIG. 1G attached to the vertebra 102A, wherein the tissue spreader 122 remains employed and the guide wire 106 is removed. FIG. 1I is a schematic of the tissue spreader 122 of FIG. 1H removed, while a second pedicle screw 104B has been coupled to the pedicle screw 104A of FIG. 1H via an immobilization rod 154 as is known in the art. The second pedicle screw 104B may be coupled to the vertebrae 102B with a pedicle screw attachment 156B using the pedicle screw system 126 in an approach similar to the approach used with pedicle screw 104A and vertebra 102A as discussed above. In this manner, the immobilization system 100 may be secured to vertebrae 102A, 102B using the pedicle screw system 126.

Figures 4A, 4B:
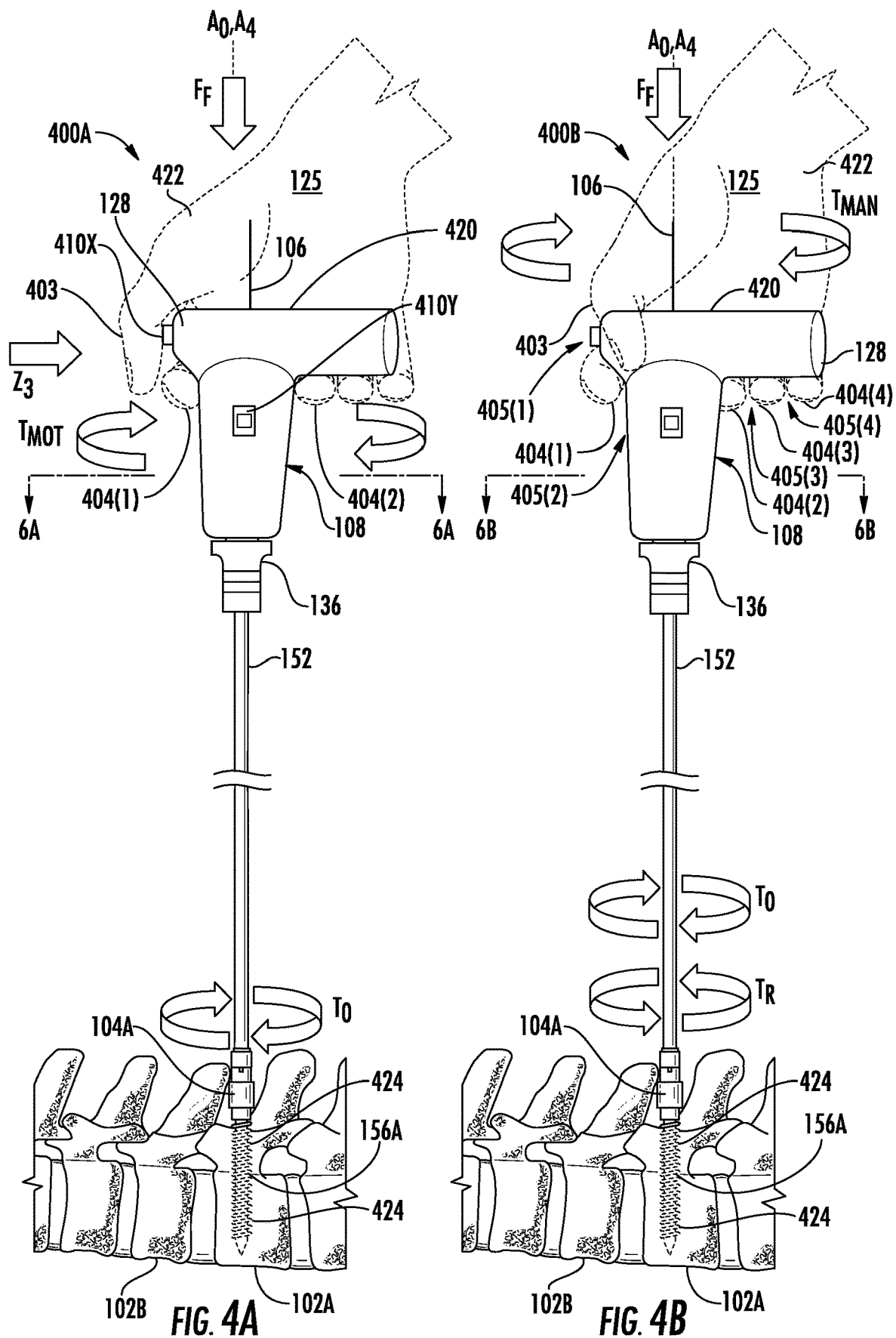
FIGS. 4A and 4B are side views of the multi-mode torque driver of FIG. 2 in a power mode and a manual mode, respectively, moving the pedicle screw relative to the vertebra to manage pedicle screw attachment.
Figure 4C:
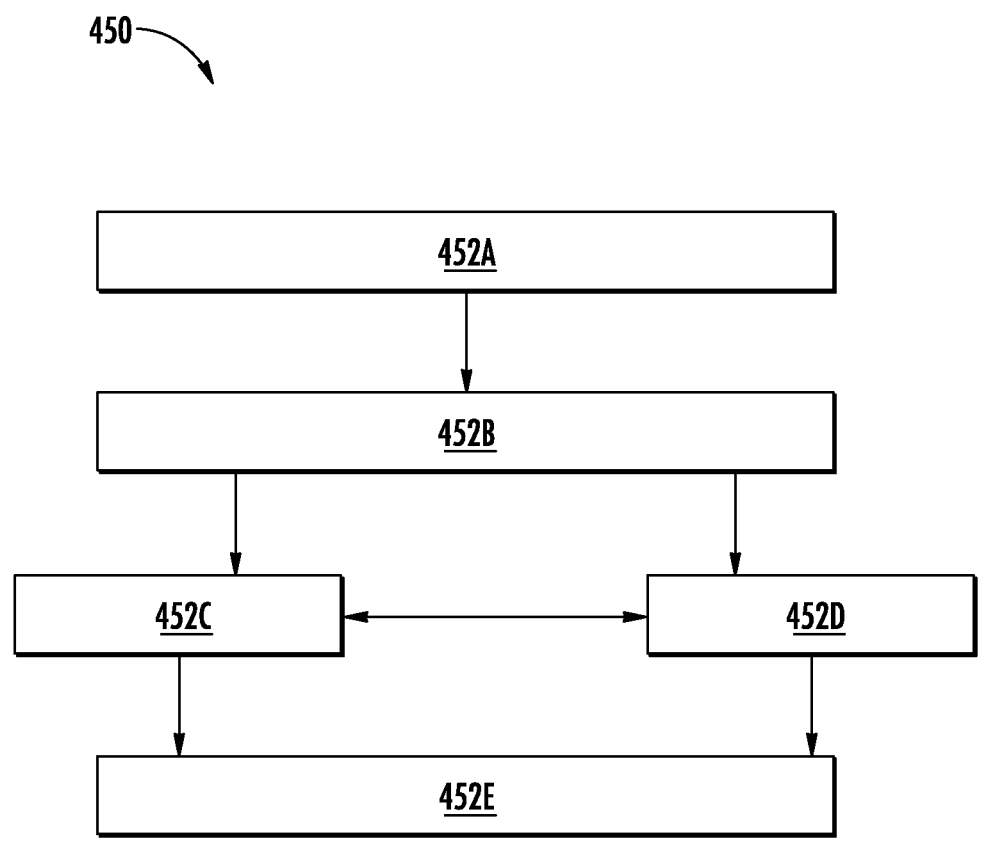
FIG. 4C is a flowchart of an exemplary method for managing the pedicle screw attachment with the vertebrae of FIG. 4A.

Now that the process for securing the immobilization system 100 has been described, details of operating the multi-mode torque driver 108 are now provided. The multi-mode torque driver 108 of the pedicle screw system 126 transmits a system torque T0 to the pedicle screw 104A coupled thereto via the screw interface 152, so that the pedicle screw attachment 156A may be managed relative to the vertebra 102A. FIGS. 4A and 4B are side views of the multi-mode torque driver 108 of FIG. 2 in a power mode 400A and a manual mode 400B, respectively, moving the pedicle screw 104A relative to the vertebrae 102A to manage the pedicle screw attachment 156A. Further, FIG. 4C is a flowchart of an exemplary method 450 for managing the pedicle screw attachment 156A with the vertebra 102A of FIG. 1F. The method 450 is now discussed using the terminology discussed above in relation to the operations 452A through 452E as depicted in FIG. 4C. In this manner, the user 125 may conveniently select combinations of the power mode 400A and the manual mode 400B of the multi-mode torque driver 108 during the insertion or retraction of the pedicle screw 104A.

In order to prepare the pedicle screw system 126 for either the power mode 400A or the manual mode 400B, the user 125 may grasp the main body 128 of the multi-mode torque driver 108 and couple the pedicle screw 104A to the pedicle screw system 126 (operation 452A of FIG. 4C). For the embodiment of the main body 128 shown in FIG. 2, the user 125 may grasp the main body 128 with the output rotational axis A0 of the multi-mode torque driver 108 disposed within interdigital spaces 405(2)-405(4) between adjacent ones of the fingers 404(1)-404(4) of the user 125. In this manner, the user 125 establishes an ergonomic coupling with the multi-mode torque driver 108 that enables a high degree of control of the pedicle screw system 126 and facilitates a high degree of tactile feedback for precise monitoring of the pedicle screw attachment 156A when a manual mode 400B is selected by the user 125.

While grasping the main body 128, the method 450 may also include the user 125 threading the guide wire 106 through the pedicle screw 104A and the pedicle screw system 126 via the passageways 304, 417 and the inner space 146 as well as abutting a male thread 424 of the pedicle screw 104A against the vertebra 102A (operation 452B of FIG. 4C). In this manner, the pedicle screw system 126 may be prepared to enter either the power mode 400A or the manual mode 400B.

Upon the user 125 selecting the power mode 400A to gain high efficiency at the expense of lower tactile feedback, the method 450 further includes at least partially moving the pedicle screw 104A relative to the vertebra 102A by applying the system torque T0 to the pedicle screw 104A in the power mode 400A (operation 452C of FIG. 4C). The user 125 may enter the power mode 400A by generating, with a motor assembly 401 (FIG. 2) disposed in the main body 128, a motorized torque $T_{MOT}$ and applying the motorized torque $T_{MOT}$ to the anti-backdrive unit 130 of the multi-mode torque driver 108. The motor assembly 401 may generate the motorized torque $T_{MOT}$ when at least one switch 410X, 410Y (FIG. 3A) of the multi-mode torque driver 108 is activated by the user 125. The system torque T0 includes the motorized torque $T_{MOT}$ in the power mode 400A. Then at least one switch 410X, 410Y may be conveniently disposed within the main body 128 to facilitate one-hand operation by the user 125. In the embodiment of the main body 128, the at least one switch 410X, 410Y may be disposed in the main body 128 for convenient one-hand operation. Once generated, the motorized torque $T_{MOT}$ becomes available to the anti-backdrive unit 130 at an output interface 412 of the motor assembly 401 (FIG. 2). In this manner, the power mode 400A is initiated by generating the motorized torque $T_{MOT}$.

Moreover, during the power mode 400A, the pedicle screw 104A receives the motorized torque $T_{MOT}$ as the system torque T0 of the multi-mode torque driver 108. In this regard, the output interface 412 of the motor assembly 401 engages with and transfers the motorized torque $T_{MOT}$ to the output element 414 of the anti-backdrive unit 130 without mechanical interference from at least one locking element 416(1)-416(N3) of the anti-backdrive unit 130 (FIG. 2). In the absence of this mechanical interference, the motorized torque $T_{MOT}$ is transferred to the output element 414 that is, in turn, coupled to the adapter chuck 136. As the adapter chuck 136 is rotationally coupled to the pedicle screw 104A through the screw interface 152, the pedicle screw 104A receives the motorized torque $T_{MOT}$ as the system torque T0 that causes the pedicle screw 104A to rotate. As the male thread 424 of the pedicle screw 104A abuts against the vertebra 102A, the pedicle screw 104A is inserted into (or retracted from) the vertebra 102A as the pedicle screw 104A rotates in response to the system torque T0 applied. In this manner, the pedicle screw attachment 156A with the vertebra 102A may be managed by inserting or retracting the pedicle screw 104A using the power mode 400A.

With reference back to FIG. 4A, it is noted that the efficiency of the movement of the pedicle screw 104A may be further facilitated by applying the feed force $F_F$ with a palm 420 of a hand 422 of the user 125 upon the main body 128. The feed force $F_F$ may be applied in the power mode 400A or the manual mode 400B. In this manner, the feed force $F_F$ may be applied parallel with the output rotational axis A0 and the guide wire 106 for accuracy and efficiency of the movement of the pedicle screw 104A.

In contrast to the efficiency provided by the power mode 400A, the user 125 may select the manual mode 400B based on several factors. For example, when confirming the strength and long-term stability of the pedicle screw attachment 156A with the vertebra 102A, the user 125 may select the manual mode 400B. The manual mode 400B involves the application of the manual torque $T_{MAN}$ to the main body 128 by the user 125 as the user 125 monitors changes in the resistance torque $T_R$ which opposes the manual torque $T_{MAN}$. As shown in FIG. 4B, the resistance torque $T_R$ is a measure of the strength and stability of the pedicle screw attachment 156A that is, as discussed above, formed by at least one of friction and mechanical interference between the pedicle screw 104A and the vertebra 102A and can be more easily perceived by the user 125 as tactile feedback during the manual mode 400B, than occurring in response to the motorized torque $T_{MOT}$ during the power mode 400A. A higher value of the resistance torque $T_R$ may be generally associated with a stronger and more stable quality of the pedicle screw attachment 156A. Accordingly, when the user 125 has high confidence in the pedicle screw attachment 156A, then the user 125 may select the power mode 400A for efficient movement of the pedicle screw 104A relative to the vertebra 102A. In this manner, the user 125 may alternate between the power mode 400A and the manual mode 400B to achieve the pedicle screw attachment 156A that may be more efficiently created while avoiding high failure rates of the pedicle screw attachment 156A.

With reference back to FIG. 4C, the method 450 also includes at least partially moving the pedicle screw 104A relative to the vertebra 102A by applying the system torque T0 to the pedicle screw 104A in the manual mode 400B (operation 452D of FIG. 4C). Specifically, the user may enter the manual mode 400B by applying the manual torque $T_{MAN}$ to the main body 128 when the pedicle screw 104A is coupled with the pedicle screw system 126 and the anti-backdrive unit 130 is free of the motorized torque $T_{MAN}$ from the motor assembly 401. In response to a resistance to rotation offered by the pedicle screw 104A coupled to the pedicle screw system 126 and held initially in place by an abutment against the vertebra 102A, the output element 414 of the anti-backdrive unit 130 initially rotates relative to the output interface 412 of the motor assembly 401. Initial rotation is possible, because the output element 414 is free of the motorized torque $T_{MOT}$. This initial rotation causes the locking elements 416(1)-416(N3) to lock the output interface 412 of the motor assembly 401 relative to the main body 128, which then stops the rotation of the output element 414 relative to the main body 128 and facilitates the manual torque $T_{MAN}$ to be transmitted through the adapter chuck 136 as the system torque T0 for the pedicle screw 104A via the output element 414. Accordingly, as the male thread 424 of the pedicle screw 104A abuts against the vertebra 102A, the pedicle screw 104A is inserted into or retracted from the vertebra 102A as the pedicle screw 104A rotates in response to the system torque T0 applied. In this manner, the pedicle screw 104A may be inserted (or retracted) using the manual mode 400B.

Figures 1, 4D:
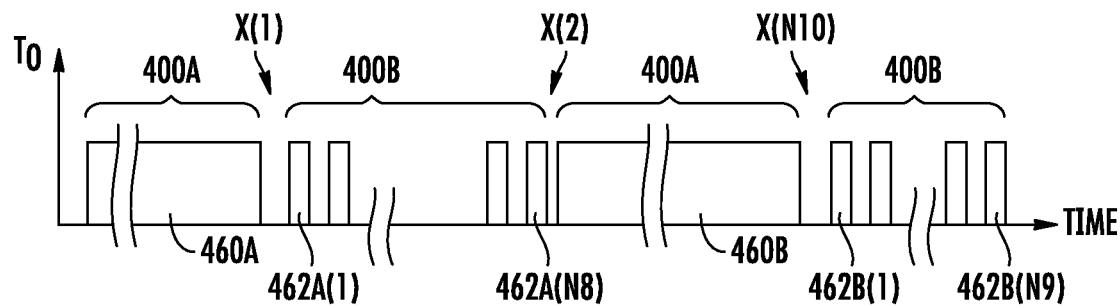
Figures 2, 4D:
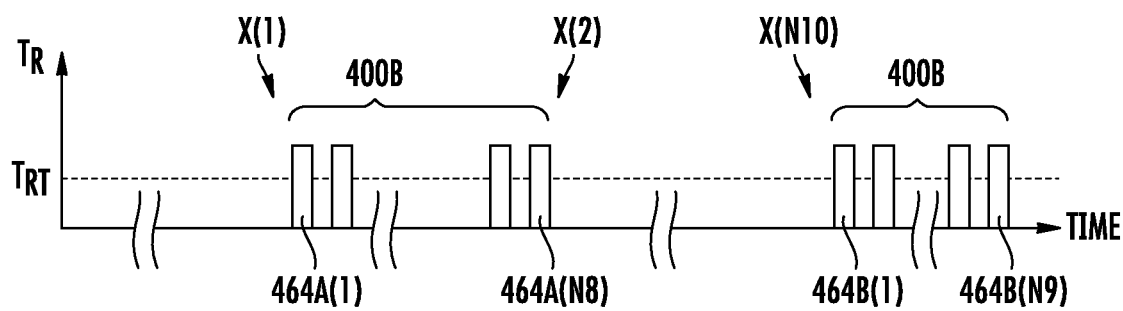

The multi-mode torque driver 108 is configured to facilitate decisions regarding transitions between the power mode 400A and the manual mode 400B. In this regard, FIGS. 4D-1 and 4D-2 are exemplary graphs of the system torque T0 produced by the multi-mode torque driver 108 of FIG. 4A and the resistance torque $T_R$ provided to the multi-mode torque driver 108, respectively, over an exemplary time period during the power mode 400A and the manual mode 400B. FIG. 4D-1 illustrates at least one power instance 460A, 460B of the power mode 400A producing the system torque T0, including the motorized torque $T_{MOT}$. The system torque T0 is illustrated as constant during each of the power modes 400A, but in other embodiments of the multi-mode torque driver 108 the system torque T0 may be variable between multiple non-zero levels. Also, during the time period, the system T0 may include manual applications 462A(1)-462A(N8) of the manual torque $T_{MAN}$ that are applied by the user 125 between the power instances 460A, 460B, and manual applications 462B(1)-462B(N9) of the manual torque $T_{MAN}$ subsequent to the power instance 460B. Each of the manual applications 462A(1)-462A(N8), 462B(1)-462B(N9) represent sequential applications of the manual torque $T_{MAN}$ applied to the pedicle screw 104A as the pedicle screw 104A is rotated during management of the pedicle screw attachment 156A. The user 125 performs transitions X(1)-X(N10) between the power mode 400A and the manual mode 400B based on efficiency and the quality of the pedicle screw attachment 156A. The quality (e.g., strength and stability) of the pedicle screw attachment 156A may be at least partially measured as the resistance torque $T_R$ available to be perceived by the user 125 through the main body 128 during the manual mode 400B. FIG. 4D-2 illustrates the resistance torque $T_R$ generated during the manual mode 400B illustrated in FIG. 4D-1. The observations 464A(1)-464A(N8) of the resistance torque $T_R$ generated immediately subsequent to the transition X(1) exceeds a resistance torque threshold $T_{RT}$ and this may result in a higher confidence that the pedicle screw attachment 156A may be strong and stable. The user 125 may subjectively establish the resistance torque threshold $T_{RT}$ based on experience and may be a qualitative or quantitative value, for example, one (1) Newton-meter. Accordingly, the user 125 may initiate the transition X(2) from manual mode 400B to power mode 400A based on observations 464A(1)-464A(N8) of the resistance torque $T_R$ received immediately subsequent to the transition X(1).

Moreover, the user 125 may continue with the power mode 400A during the power instance 460B as long as there is confidence that there is a strong and stable attachment. As shown in FIG. 4D-1, the transition X(N10) from the power mode 400A to the manual mode 400B may be initiated by the user 125 to assist in determining whether the pedicle screw attachment 156A with the vertebra 102A remains strong and stable. As is depicted in the associated FIG. 4D-2, observations 464B(1)-464B(N9) of the resistance torque $T_R$ generated immediately after the transition X(N10) exceeds the resistance torque threshold $T_{RT}$ and this may indicate that the pedicle screw attachment 156A is strong and stable. The user 125 may engage in various combinations of the transitions X(1)-X(N10) to ensure high confidence that a strong and stable quality of the pedicle screw attachment 156A has been achieved.

Figures 1, 4E:
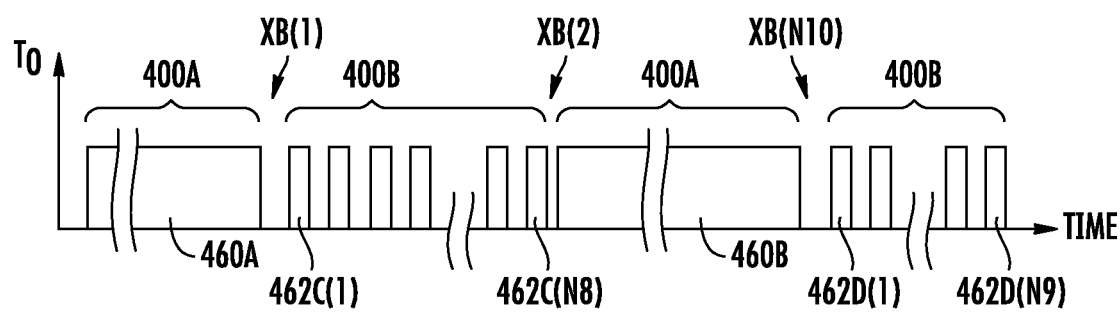
Figures 2, 4E:
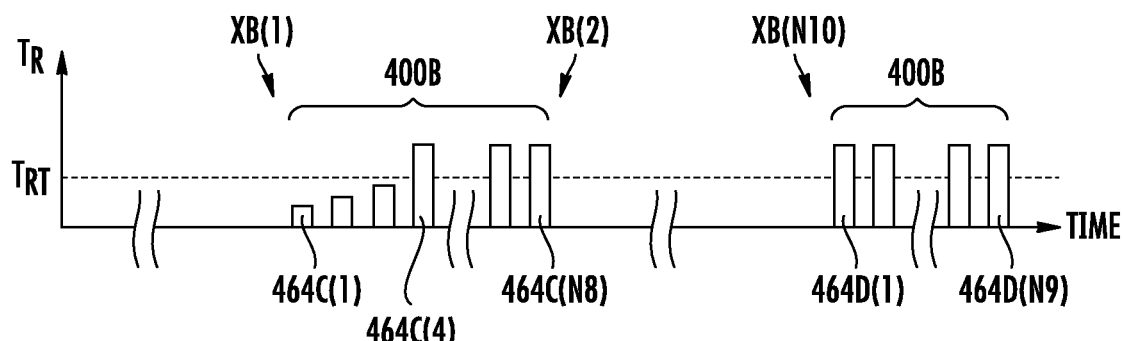

In contrast, FIGS. 4E-1 and 4E-2 are exemplary graphs of system torque T0 produced by the multi-mode torque driver 108 of FIG. 4A and resistance torque $T_R$ provided to the multi-mode torque driver 108, respectively, over an exemplary second time period during the power mode 400A and the manual mode 400B illustrating the resistance torque $T_R$ temporarily below the resistance torque threshold $T_{RT}$. During this second time period, the user 125 initiates a transition XB(1) from the power mode 400A to the manual mode 400B, a transition XB(2) from the manual mode 400B to the power mode 400A, and a transition XB(N10) from the power mode 400A to the manual mode 400B. The manual applications 462C(1)-462C(N8), 462D(1)-462D(N9) of the system torque T0 in the manual mode 400B may respectively result in the resistance torque $T_R$ as represented by the observations 464C(1)-464C(N8), 464D(1)-464D(N9). The observations 464C(1)-464C(3) are below the resistance torque threshold $T_{RT}$. Upon receiving the observations 464C(1)-464C(3), the user 125 may decide that the confidence level in the strength and stability of the pedicle screw attachment 156A is not high. In response, the user 125 may delay the transition XB(2) to the power mode 400A and thereby receive additional observations 464C(4)-464C(N8) to determine whether the confidence level may have increased or take other responsive actions (e.g., use thicker pedicle screw and/or change desired trajectory A1). In this exemplary situation exhibited in FIG. 4E-2, the additional observations 464C(4)-464C(N8) exceed the resistance torque threshold $T_{RT}$, and so the confidence level may be increased where the user 125 initiated the transition XB(2) from the manual mode 400B to the power mode 400A. The observations 464C(4)-464C(N8) also exceeded the resistance torque threshold $T_{RT}$ and these observations 464C(4)-464C(N8) may indicate that the pedicle screw attachment 156A is strong and stable.

In summary, automatic transitions between the power mode 400A and the manual mode 400B are made possible with the anti-backdrive unit 130 when the pedicle screw 104A is coupled with the pedicle screw system 126. The automatic transition to the power mode 400A is initiated by transmitting the motorized torque $T_{MOT}$ from the motor assembly 401 to the anti-backdrive unit 130. Alternatively, the automatic transition to the manual mode 400B may be initiated by the user 125 by applying the manual torque $T_{MAN}$ to the main body 128 while the pedicle screw 104A is coupled to the output element 414 of the anti-backdrive unit 130 and the pedicle screw 104A is receiving rotational resistance from the vertebra 102A in the absence of the motorized torque $T_{MOT}$. The automatic transitions expedite the surgical process and promote surgical accuracy as the user 125 may use the power mode 400A for efficiency yet conveniently transition, when desired, to and from the manual mode 400B to confirm the pedicle screw attachment 156A to the vertebra 102A is strong and stable. The automatic transitions also minimize a quantity of switches or transitions needed for the user 125 to control the multi-mode torque driver 108.

With reference back to FIG. 4C, the method 450 also includes decoupling the pedicle screw 104A from the pedicle screw system 126 once the pedicle screw attachment has been achieved (Operation 452E of FIG. 4C). The pedicle screw 104A may be disengaged from the screw interface 152 of the pedicle screw system 126 once the movement of the pedicle screw 104A is no longer necessary for the pedicle screw attachment 156A. As part of this detachment the pedicle screw system 126 may also be disengaged from the guide wire 106. Disengaging the pedicle screw system 126 from the guide wire 106 may include having the user 125 move the pedicle screw system 126 away from the vertebra 102A as the guide wire 106 remains attached to the vertebra 102A. As a consequence of moving the pedicle screw system 126, the guide wire 106 may slide out from the pedicle screw 104A and the pedicle screw system 126 resulting in disengagement from the guide wire 106. In this manner, the pedicle screw attachment 156A may be completed and the tissue spreader 122 and guide wire 106 removed from the vertebra 102A. The second pedicle screw 104B may be similarly attached to the vertebra 102B, and the immobilization rod 154 may be later fastened to the pedicle screws 104A, 104B to form the immobilization system 100 (FIG. 1I). In this manner, the vertebrae 102A, 102B may be fused using an immobilization system 100 created by use of the multi-mode torque driver 108.

Now that the method 450 of the pedicle screw system 126 has been introduced, details of the components of the multi-mode torque driver 108 are now provided. FIGS. 5A through 5H are a front view, top view, bottom view, rear view, left side view, right side view, left side sectional view, and exploded view, respectively, of the multi-mode torque driver 108 of the pedicle screw system 126 of FIG. 2. The multi-mode torque driver 108 may include the motor assembly 401, the anti-backdrive unit 130, the battery 134, the main body 128, the adapter chuck 136, and the switches 410X, 410Y. Details of each of these will now be sequentially discussed.

The motor assembly 401 provides motor rotational energy, including the motorized torque $T_{MOT}$ during the power mode 400A. The rotational energy includes a motorized torque $T_{MOT}$ in a range from two (2) Newton-meters to ten (10) Newton-meters and a rotational speed in a second range from fifty (50) RPM to two hundred (200) RPM. The motorized torque $T_{MOT}$ is provided to be sufficient to move the pedicle screw 104A along the desired trajectory A1 of the guide wire 106 as the male thread 424 of the pedicle screw 104A abuts against the vertebrae 102A. The rotation speed may be configured to insert the pedicle screw 104A into the vertebrae 102A in less than thirty (30) seconds and preferably approximately fifteen (15) seconds when the pedicle screw 104A requires less than thirty (30) rotations to form the pedicle screw attachment 156A. It is noted that establishing the pedicle screw attachment 156A may involve other ancillary tasks (e.g., tapping and verifying the desired trajectory A1) that may take up additional time that may not be represented in the less than thirty (30) seconds.

Moreover, the motor assembly 401 may include the motor 132 coupled to a drive train 504 to collectively produce the motorized torque $T_{MOT}$ and the rotational speed. The motor 132 may, for example, be a direct current (DC) electric motor. The motor 132 may be supplied power from the battery 134. The motor 132 may support both clockwise and counterclockwise generation of rotational energy that may be transmitted as the motorized torque $T_{MOT}$. In this manner, the motorized torque $T_{MOT}$ may be generated during the power mode 400A.

It is envisioned that in future alternative embodiments the motor 132 may supply the motorized torque $T_{MOT}$ and rotational speed without the drive train 504. However, in the embodiments illustrated herein the drive train 504 of the motor assembly 401 may include epicyclic gearing including, for example, first and second planetary gear stages 506A, 506B (FIG. 5H) to provide the high torque and appropriate rotational speed consistent with managing the pedicle screw attachment 156A. The first planetary gear stage 506A may be linked to the motor 132 with a sun gear 680 of an intermediate element 508. The first planetary gear stage 506A may include a plurality of first planet gears 510A(1)-510A(N4) in communication with annulus gear teeth 512 of an intermediate sleeve 513 of the main body 128 and supported by a carrier backplane 514. An output sun gear 516 of the first planetary gear stage 506A may be input into a second planetary gear stage 506B. The second planetary gear stage 506B may include a plurality of second planet gears 510B(1)-510B(N5) in communication with the annulus gear teeth 512 of the main body 128 and supported by the output interface 412 of the motor assembly 401. Each of the first and second planetary gear stages 506A, 506B may have a ratio in a range from 1:9 to 1:13, and preferably 1:11. The first and second planetary gear stages 506A, 506B may be made of a strong rigid material, for example, a metal or plastic (e.g., polyetherimide provided by SABIC of Pittsfield, Mass.). In this manner, the motorized torque $T_{MOT}$ may be provided to the anti-backdrive unit 130 by the output interface 412 of the motor assembly 401 during the power mode 400A.

Figure 5A:
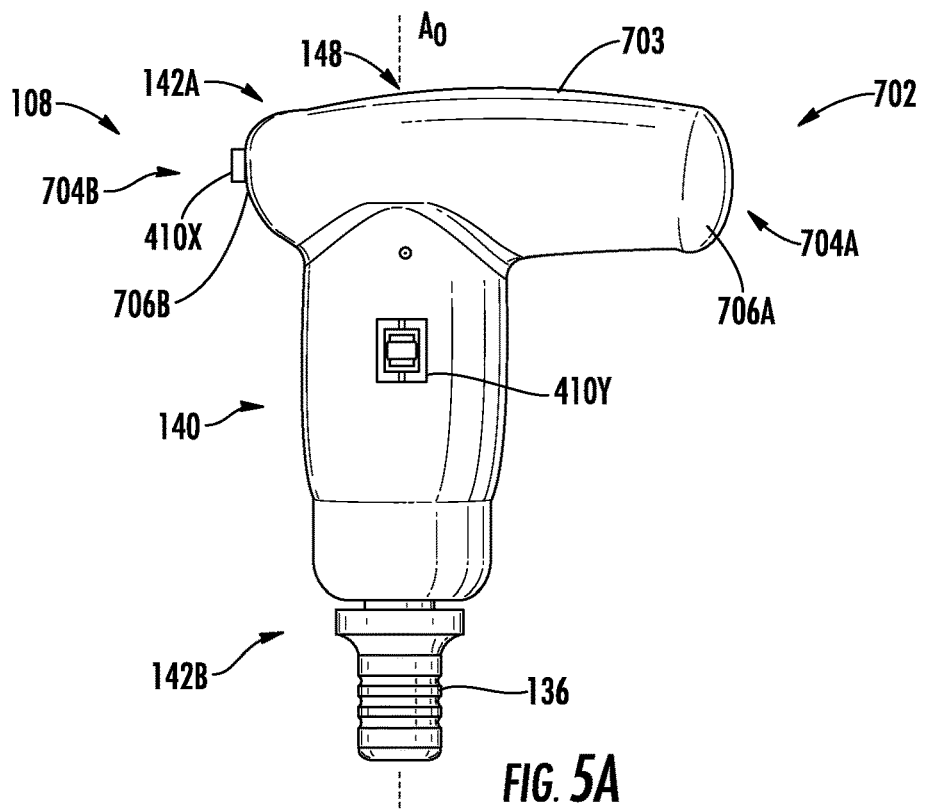
FIGS. 5A through 5H are a front view, top view, bottom view, rear view, left side view, right side view, left side sectional view, and exploded view, respectively, of the multi-mode torque driver of FIG. 2.
Figure 5B:
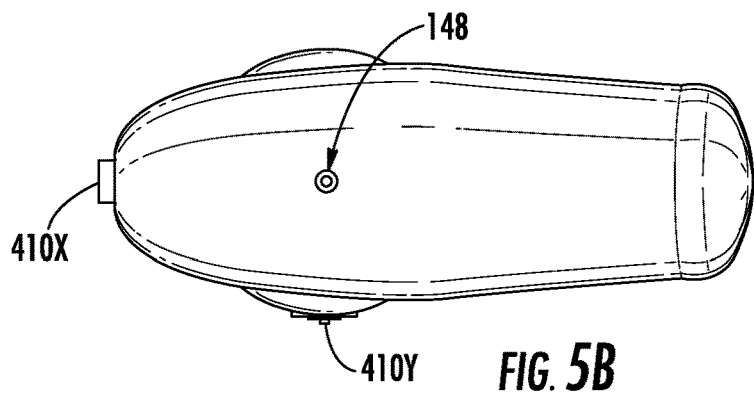
Figure 5C:
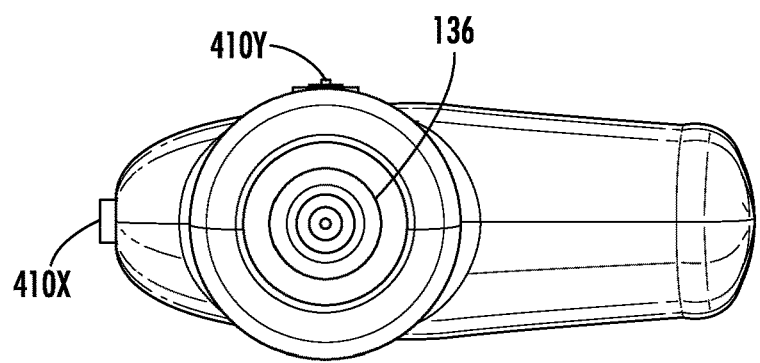
Figure 5D:
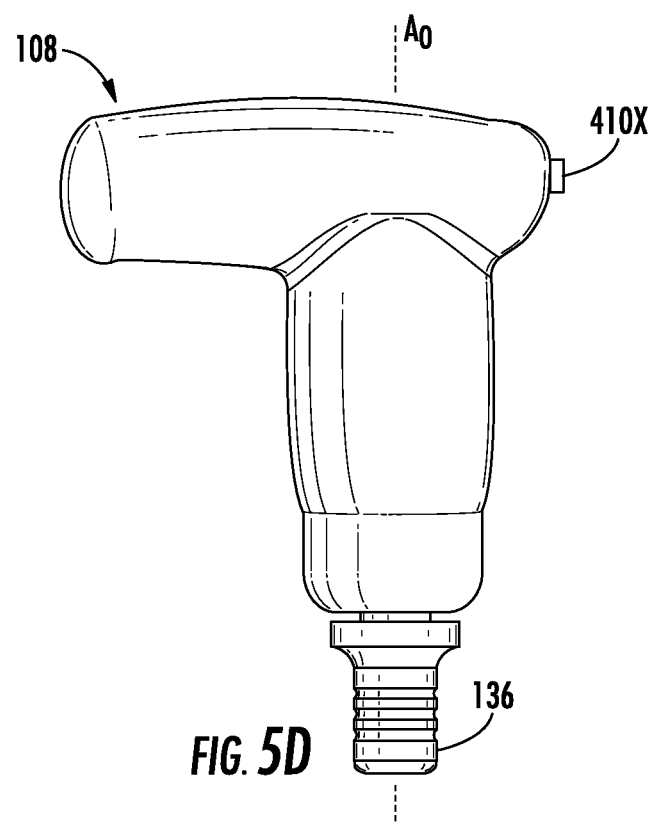
Figure 5E:
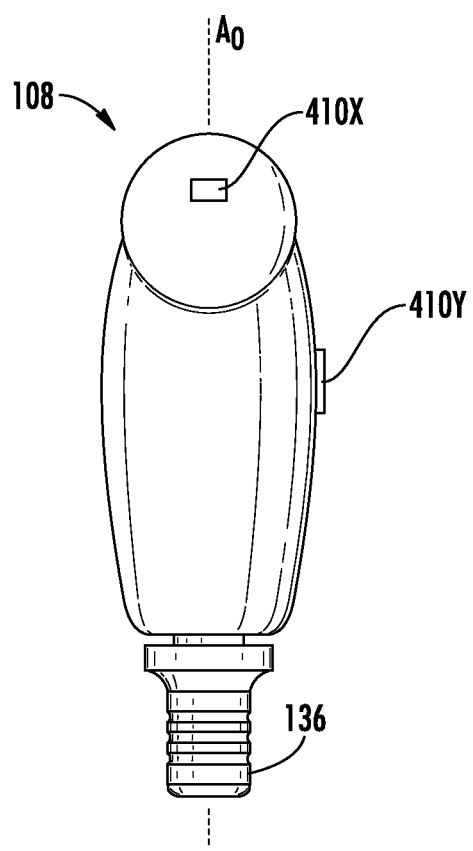
Figure 5F:
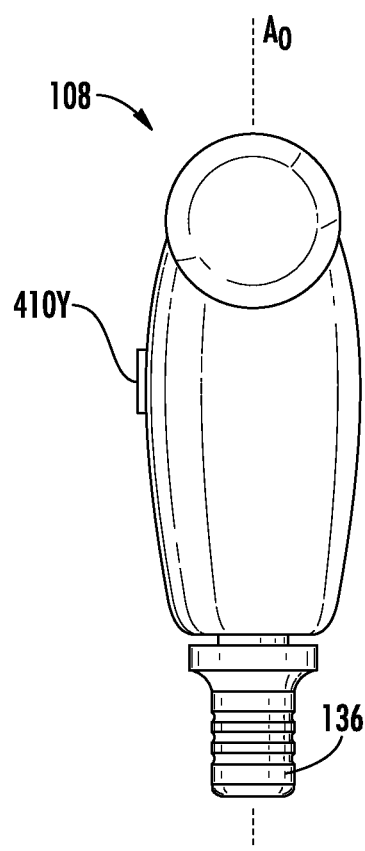
Figure 5G:
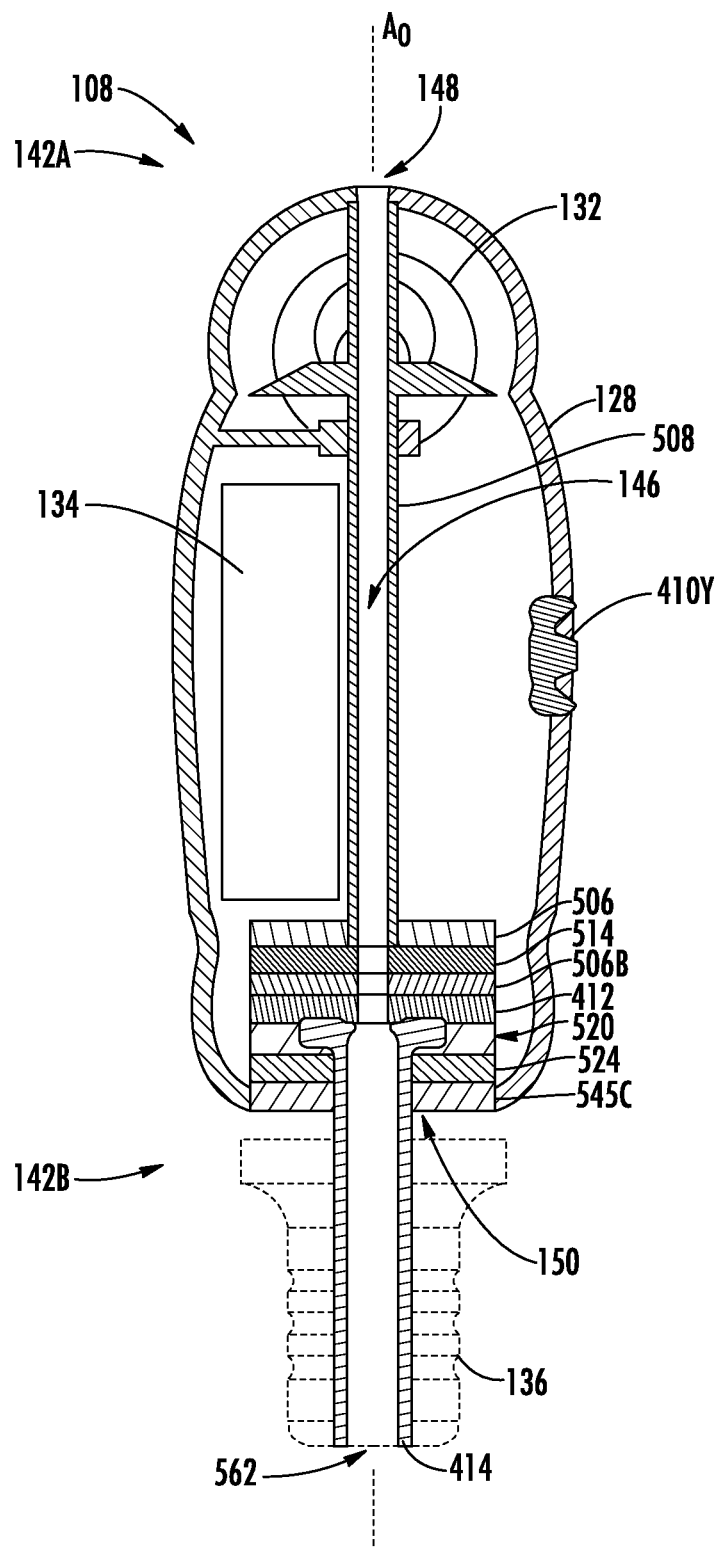
Figure 5H:
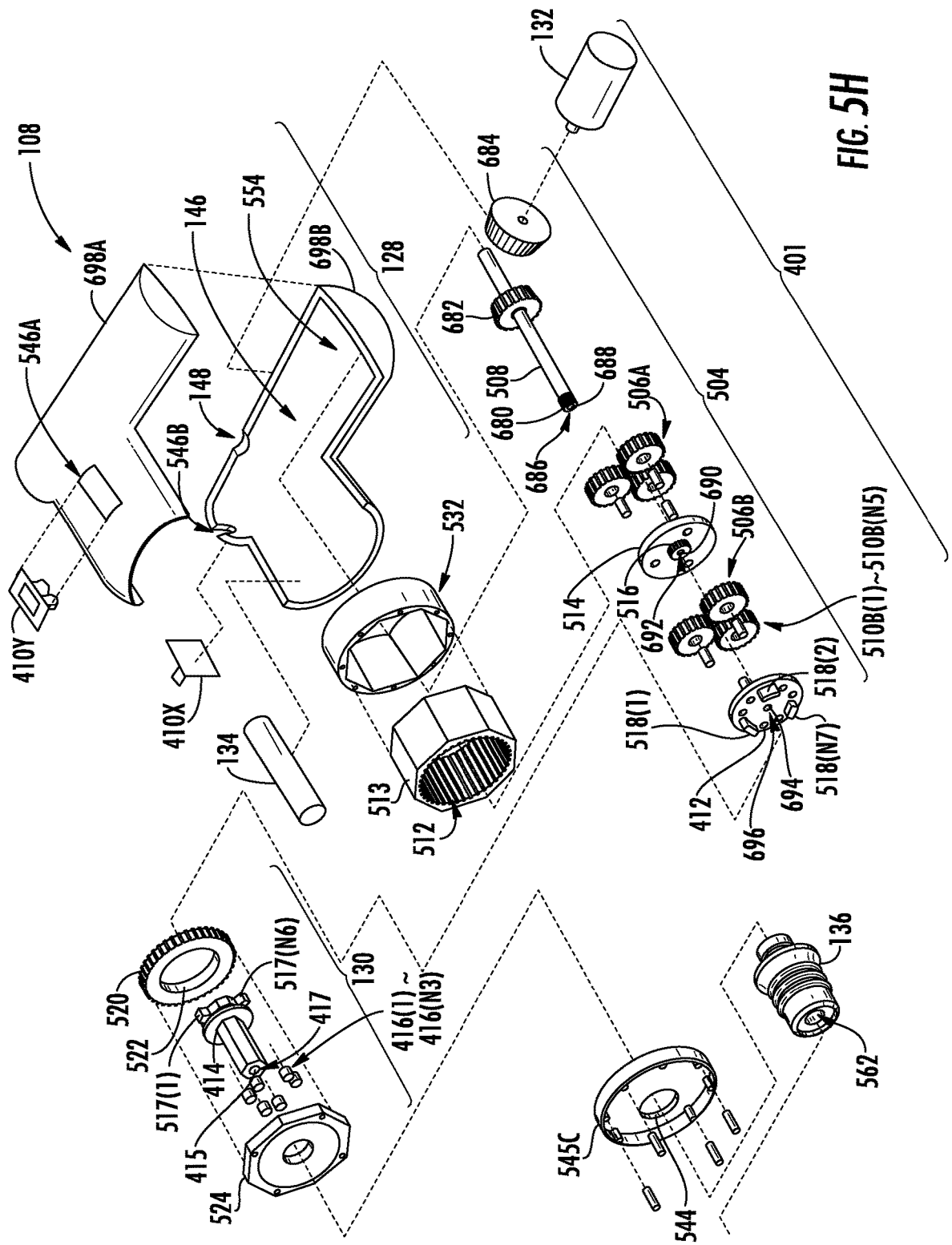

As shown in FIG. 5H, the intermediate element 508 may include the sun gear 680 and a bevel gear 682. The sun gear 680 may be coupled to the first planetary gear stage 506A and connected to the bevel gear 682. The bevel gear 682 may be coupled to a second bevel gear 684 to receive $T_{MOT}$ from the motor 132 arranged at the transmission angle θ (theta) relative to the output rotational axis A0 of the multi-mode torque driver 108. Further, the intermediate element 508 may include an inner surface 686 forming a passageway 688 through the bevel gear 682 and the sun gear 680 to facilitate the threading of the guide wire 106 through the inner space 146 of the multi-mode torque driver 108.

The carrier backplane 514 and the output sun gear 516 may also facilitate the threading of the guide wire 106. The carrier backplane 514 and the output sun gear 516 may include an inner surface 690 forming a passageway 692 through the carrier backplane 514 and the output sun gear 516. The passageway 692 is configured to receive the guide wire 106 as the guide wire 106 is being threaded through the multi-mode torque driver 108. In this manner, the guide wire 106 may be threaded through the carrier backplane 514 and the output sun gear 516 while being threaded through the inner space 146. It is also noted that gears may be spaced apart within each of the first and the second planetary gear stages 506A, 506B so that these gears do not obstruct the guide wire 106 as the guide wire 106 is threaded through the multi-mode torque driver 108.

The output interface 412 may also facilitate the threading of the guide wire 106 through the inner space 146 of the multi-mode torque driver 108. The output interface 412 may include an inner surface 694 forming a passageway 696 through the output interface 412. The passageway 696 is configured to receive the guide wire 106 when the guide wire 106 is being threaded through the multi-mode torque driver 108. In this manner, the guide wire 106 may be threaded through the output interface 412.

With continued reference to FIGS. 5A through 5H, the anti-backdrive unit 130 enables the system torque T0 to be transmitted to the pedicle screw 104A, wherein the system torque T0 includes the motorized torque $T_{MOT}$ in the power mode 400A and the $T_{MAN}$ in the manual mode 400B. The anti-backdrive unit 130 includes the output element 414, the locking elements 416(1)-416(N3), collar portion 524, and the housing portion 520. These components of the anti-backdrive unit 130 function cooperatively with the main body 128 and the output interface 412 of the motor assembly 401 to facilitate the transition between the power mode 400A and the manual mode 400B. Specifically, the output element 414 of the anti-backdrive unit 130 includes radial elements 517(1)-517(N6) and the output interface 412 of the motor assembly 401 includes post portions 518(1)-518(N7) which may rotate concentrically with the locking elements 416(1)-416(N3) around the output rotational axis A0 and within an inner circumferential surface 522 of a housing portion 520. The housing portion 520 and the collar portion 524 may be statically coupled to the main body 128. The housing portion 520 and the output element 414 in combination with the collar portion 524 and the output interface 412 may form at least one enclosure to contain the locking elements 416(1)-416(N3). The position of the locking elements 416(1)-416(N3) relative to the radial elements 517 (1)-517(N6) and the post portions 518(1)-518(N7) determines whether the multi-mode torque driver 108 operates in the power mode 400A or the manual mode 400B.

Details of the anti-backdrive unit 130 are now discussed. In this regard, FIGS. 6A and 6B that are partial top sectional views parallel to the output rotational axis A0 of the multi-mode torque driver 108 in FIGS. 4A and 4B, respectively, illustrating the anti-backdrive unit 130 operating in the power mode 400A and the manual mode 400B. As shown in the exemplary power mode 400A illustrated in FIG. 6A, the post portions 518(1)-518(N7) of the output interface 412 of the motor assembly 401 may be rotated about the output rotational axis A0 by the motorized torque $T_{MOT}$. The post portions 518(1)-518(N7) abut against and urge the locking elements 416(1), 416(3), 416(5) to rotate about the output rotational axis A0 in the same direction while being guided along a circumferential path by the inner circumferential surface 522. In response to being urged, the locking elements 416(1), 416(3), 416(5) abut against the radial elements 517(1)-517(N6) of the output element 414 of the anti-backdrive unit 130 to transmit the motorized torque $T_{MOT}$ to the pedicle screw 104A as the system torque T0 through the output element 414. Also, the locking elements 416(2), 416(4), 416(N3) do not offer significant resistance to the transfer of this rotational energy of the motorized torque $T_{MOT}$, because the radial elements 517(1)-517(N6) abut against and urge the locking elements 416(2), 416(4), 416 (N3) to rotate about the output rotational axis A0 in the same direction and rotational speed as the locking elements 416 (1), 416(3), 416(5). In this manner, the anti-backdrive unit 130 transfers the motorized torque $T_{MOT}$ to the pedicle screw 104A as the system torque T0 via the anti-backdrive unit 130.

The power mode 400A enables the motorized torque $T_{MOT}$ to be transferred to the output element 414 without the locking elements 416(1)-416(N3) locking the output element 414 relative to the inner circumferential surface 522 that is statically coupled to the main body 128. In the output element 414 of FIG. 6A the radial elements 517(1)-517(N6) are connected by an external surface 528. This external surface 528 is arranged to be non-concentric with the inner circumferential surface 522 when rotating about the output rotational axis A0. Accordingly, locking may be avoided by maintaining the locking elements 416(1)-416(N3) in positions where the localized separations between the inner circumferential surface 522 and the external surface 528 are greater than the respective widths D0 of the locking elements 416(1)-416(N3) at those positions. By virtue of the non-concentricity, it is noted that nearest the radial elements 517(1)-517(N6) the localized separation is a distance D1 and increases to a local separation of distance D2 at positions further from the radial elements 517(1)-517(N6). As is shown in the power mode 400A illustrated in FIG. 6A, locking is avoided because the locking elements 416(1)-416 (N3) are maintained in positions against the radial elements 517(1)-517(N6) where the localized separations between the inner circumferential surface 522 and the external surface 528 are greater than the respective widths D0 of the locking elements 416(1)-416(N3). In this manner, the motorized torque $T_{MOT}$ is most efficiently transmitted as the system torque T0 through the anti-backdrive unit 130 in the power mode 400A.

In contrast, in the exemplary manual mode 400B illustrated in FIG. 6B, the output element 414 of the anti-backdrive unit 130 receives the manual torque $T_{MAN}$ and rotates about the output rotational axis A0. As the motor assembly 401 remains inactive (free of motorized torque $T_{MOT}$) during the manual mode 400B, the post portions 518(1)-518(N7) are urged to move circumferentially about the output rotational axis A0 as the radial elements 517(1)-517(N6) abut against the post portions 518(1)-518(N7) through the locking elements 416(2), 416(4), 416(N3). The locking elements 416(1), 416(3), 416(5) establish a lock preventing the output element 414 from moving relative to the inner circumferential surface 522 which is static relative to the main body 128, because the housing portion 520 is statically coupled to the main body 128 via the intermediate sleeve 513. This locking in the form of mechanical interference occurs, because the post portions 518(1)-518(N7) are not purposely sized circumferentially long enough to displace these locking elements 416(1), 416(3), 416(5) to positions where the localized separations between the inner circumferential surface 522 and the external surface 528 are greater than the respective widths D0. Instead, locking results, because the locking elements 416(1), 416(3), 416(5) are disposed in positions where the localized separation distance of D2 is no more than the widths D0 of the locking elements 416(1), 416(3), 416(5). In this manner, the locking achieved in the anti-backdrive unit 130 couples the output element 414 of the anti-backdrive unit 130 to the inner circumferential surface 522 of the housing portion 520 which statically coupled to the main body 128 during the manual mode 400B and this locking enables the manual torque $T_{MAN}$ applied by the user 125 at the gripper handle portion 702 of the main body 128 to be transmitted to the pedicle screw 104A through the anti-backdrive unit 130.

It is noted that the locking elements 416(1)-416(N3) may include either a spherical shape or cylindrical shape to easily engage and disengage with the radial elements 517(1)-517 (N6) and the post portions 518(1)-518(N7). The spherical shape or cylindrical shape also enables the locking elements 416(1)-416(N3) to efficiently move circumferentially about the output rotational axis A0 along the inner circumferential surface 522 of the housing portion 520. In this manner, the locking elements 416(1)-416(N3) enable more efficient transitions between the power mode 400A and the manual mode 400B.

Next, with reference back to FIGS. 5A through 5H, the battery 134 provides energy to the motor assembly 401 during the power mode 400A. The battery 134 provides electrical energy to be converted by the electric motor 132 to the motorized torque $T_{MOT}$. The battery 134 may be, for example, a lithium-ion polymer battery having a voltage, for example, in a range from three (3) to ten (10) volts. The battery 134 may include connectivity elements (not shown) having electrically conductive materials to transfer energy of the battery 134 to the motor 132. In this manner, the battery 134 may facilitate the generation of the motorized torque $T_{MOT}$ at the electric motor 132.

In yet another component of the multi-mode torque driver 108, the main body 128 enables the user 125 to control the pedicle screw system 126 and also may facilitate an interrelationship between the battery 134, the anti-backdrive unit 130, adapter chuck 136, and the motor assembly 401, to operate as a cohesive system. The main body 128 may include first and second halves 698A, 698B (see FIG. 5H). The "two-halves" construction may enable efficient assembly of the multi-mode torque driver 108. The main body 128 may include the center portion 140 extending from the first end 142A to the second end 142B. In addition, the main body 128 may include a gripper handle portion 702. The center portion 140 and the gripper handle portion 702 may be collectively arranged in a capital letter "T" shape (FIG. 5A). The capital "T" shape enables the main body 128 to be more easily manipulated by the user 125 in the power mode 400A and the manual mode 400B, because the capital T-shape facilitates the output rotational axis A0 to be disposed within one of the interdigital spaces 405(2)-405(4) between the fingers 404(1)-404(4) and facilitates the feed force $F_F$ to be applied by the user 125 parallel with the output rotational axis A0 to minimize wobble. Specifically, the center portion 140 extends along the output rotational axis A0 from a first end 142A to a second end 142B, wherein the center portion 140 is arranged to transfer the manual torque $T_{MAN}$ applied by the user 125 at the gripper handle portion 702 from the first end 142A to the second end 142B. In this manner, when the multi-mode torque driver 108 is coupled to the pedicle screw 104A, then the center portion 140 may serve as a conduit for the manual torque $T_{MAN}$ to be transferred between the gripper handle portion 702 connected at the first end 142A and the anti-backdrive unit 130 disposed at the second end 142B.

The gripper handle portion 702 of the main body 128 serves as the interface for the user 125 during use of the multi-mode torque driver 108. The gripper handle portion 702 includes an external gripper surface 703 shaped as a plurality of protrusions 704A, 704B attached to and extending from the first end 142A of the center portion 140 to respective ones of the distal ends 706A, 706B disposed away from the output rotational axis A0. The protrusions 704A, 704B are adapted to receive and transfer the manual torque $T_{MAN}$ from the user 125 to the first end 142A of the main body 128. The external gripper surface 703 is shaped for adjacent ones of the fingers 404(1)-404(4) of the user 125 (FIG. 4A) to wrap around respective ones of the protrusions 704A, 704B as the center portion 140 and the output rotational axis A0 are disposed between the adjacent ones of the fingers 404(1)-404(4) of the user 125 when the gripper handle portion 702 receives the manual torque $T_{MAN}$ from the user 125 in the manual mode 400B. In this manner, the user 125 may apply the manual torque $T_{MAN}$ during the manual mode 400B.

Figure 5I:
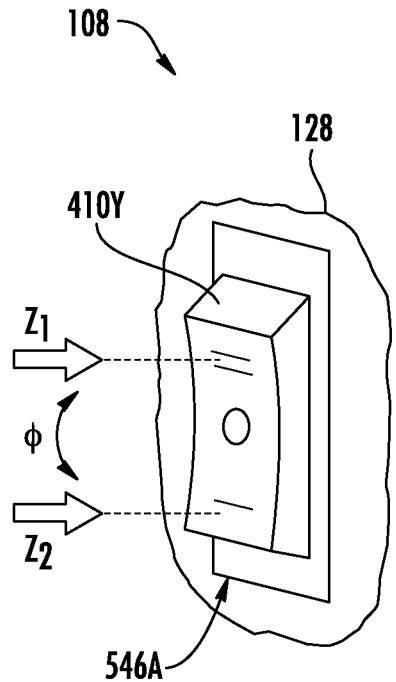
FIGS. 5I and 5J are front and left perspective views, respectively, of the front and left-side switches of a main body of the multi-mode torque driver of FIG. 2.
Figure 5J:
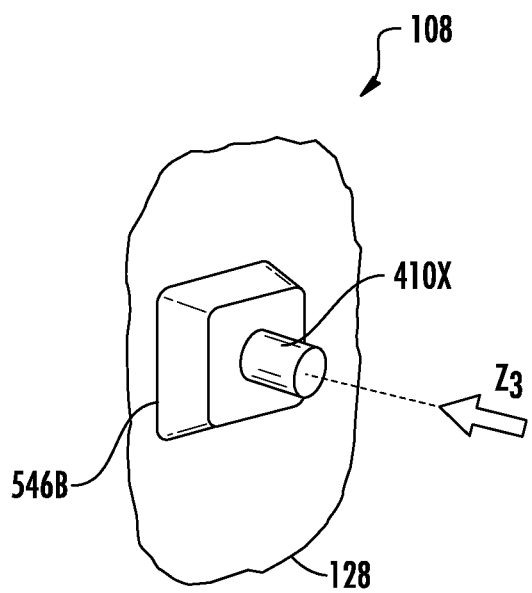

Also, the switches 410X, 410Y may operate cooperatively to control the generation of the motorized torque $T_{MOT}$. FIGS. 5I through 5J are left and right top perspective views, respectively, of the switches 410Y, 410X of the multi-mode torque driver 108. The switch 410Y may be a rocker switch type as shown in FIG. 5H capable of rotating to three angular positions according to an angle 1 (phi) by forces Z1, Z2 applied by the user 125 to the switch 410Y. Each of the three angular positions may respectively designate for the motor assembly 401: a clockwise direction of the motorized torque, an off position, and a counterclockwise direction of the motorized torque $T_{MOT}$. The switch 410X may work in cooperation with the switch 410Y. The switch 410X may be a push button switch type configured to receive a force Z3 from the user 125. When the force Z3 is applied to the switch 410X and the switch 410Y designated either a clockwise or counterclockwise direction, then the motorized torque $T_{MOT}$ may be generated consistent with the direction designated by the switch 410Y. The switch 410X may be binary with only on and off positions corresponding to whether the force Z3 is applied. In other alternative embodiments the switch Z3 may control a level of the motorized torque $T_{MOT}$ based on an amount of the force Z3 applied to the switch 410X. In either case, the user 125 may not use the switch 410X to generate the motorized torque $T_{MOT}$ while the switch 410Y is in the off position. Thus, the switches 410X, 410Y act cooperatively with each other. In this manner, the user 125 may use the switch 410Y to control a direction of the motorized torque $T_{MOT}$ or optionally place the motor assembly 401 in an off position to prevent inadvertent generation of the motorized torque $T_{MOT}$.

Further, the inner surface 144 of the main body 128 also forms the inner space 146 connecting the at least one of the motor control ports 546A, 546B (FIG. 5H) and the output opening 150. The inner surface 144 includes a motor mounting interface 554 (FIG. 5H) configured to receive the motorized torque $T_{MOT}$ from the motor 132 when the multi-mode torque driver 108 in a power mode 400A. The motor mounting interface 554 may be arranged so that at least a portion of the motor 132 is disposed within the inner space 146 formed by the inner surface 144. In this manner, the motor 132 can be arranged relative to other components of the multi-mode torque driver.

Next, the adapter chuck 136 transmits the system torque T0 from the output element 414 of the anti-backdrive unit 130 to the screw interface 152. The adapter chuck 136 may be attached to and in rotational communication with the output element 414. The adapter chuck 136 may include a coupling opening 562 (FIG. 3B) that is concentric to the output rotational axis A0 and receives the standard connection end 300A of the screw interface 152, so that a coupling can occur to align the screw interface 152 with the output rotational axis A0. Within the coupling opening 562 the adapter chuck 136 may provide A0-type coupling compatibility or other standard coupling types (e.g., quarter inch square) to couple with the screw interface 152. It is also contemplated that the adapter chuck 136 may also include an adjustable ratchet feature (not shown) to transmit the system torque T0 in one selectable direction to minimize hand movement of the user 125 when applying the manual torque $T_{MAN}$ over multiple rotations. In this manner, the system torque may be conveyed to the pedicle screw 104A via the adapter chuck 136.

Other embodiments of the mode torque driver 108 are possible. FIGS. 7A through 7D are front sectional views of second, third, fourth, and fifth embodiments of the multi-mode torque driver 108 of FIG. 2. For clarity the terminology describing FIGS. 7A through 7D will be consistent with the terminology used previously for the multi-mode torque driver 108, and mainly only differences will be described in an effort to provide conciseness.

Figure 7A:
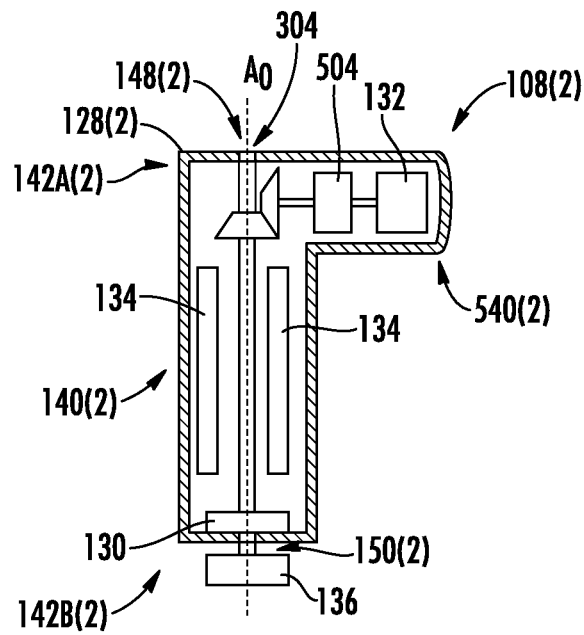
FIGS. 7A through 7D are front sectional views of second, third, fourth, and fifth embodiments of the multi-mode torque driver of FIG. 2.

Specifically, FIG. 7A illustrates a front sectional view of a multi-mode torque driver 108(2). The main body 128(2) includes a center portion 140(2) extending along the output rotational axis A0 from a first end 142A(2) to a second end 142B(2). The main body 128(2) includes a cannulation port 148(2) at the first end 142A(2) and an output opening 150(2) at the second end 142B(2) and both disposed along the output rotational axis A0. The inner surface 144(2) of the main body 128(2) forms an inner space 146(2) connecting the cannulation port 148(2) and the output opening 150(2) and forming a passageway for the guide wire 106 along the output rotational axis A0. The anti-backdrive unit 130 and the battery 134 may be disposed within the center portion 140(2) to minimize the size of the center portion 140(2) while a drive train 504(2) and the motor 132 are disposed in a protrusion 704(2) extending from the center portion 140(2) at the first end 142A(2). In this manner, guide wire capability can be provided to the multi-mode torque driver 108(2) with a minimum size of the center portion 140(2) to minimize obstructions to a visual field of the user 125 of the vertebra 102A during insertion of the pedicle screw 104A.

Figure 7B:
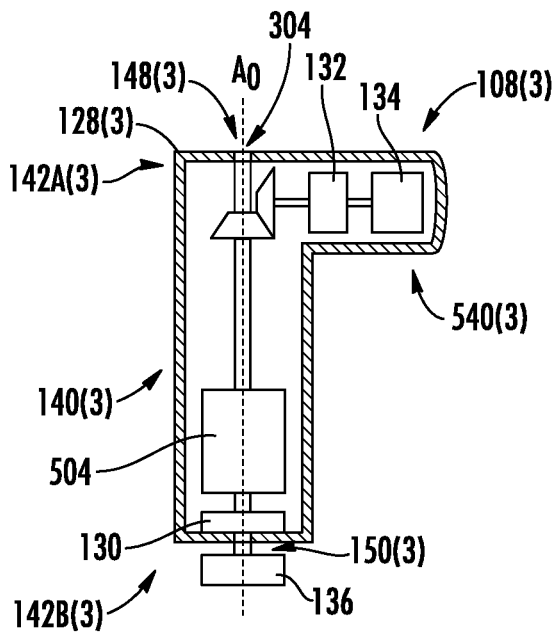

Next, FIG. 7B illustrates a front sectional view of a multi-mode torque driver 108(3). The main body 128(3) includes a center portion 140(3) extending along the output rotational axis A0 from a first end 142A(3) to a second end 142B(3). The main body 128(3) includes a cannulation port 148(3) at the first end 142A(3) and an output opening 150(3) at the second end 142B(3) and both disposed along the output rotational axis A0. The inner surface 144(3) of the main body 128(3) forms an inner space 146(3) connecting the cannulation port 148(3) and the output opening 150(2) and forming a passageway for the guide wire 106 along the output rotational axis A0. The anti-backdrive unit 130 and drive train 504(3) may be disposed within the center portion 140(3) while the battery 134 and motor 132 are disposed in a protrusion 704(3) extending from the center portion 140(3) at the first end 142A(3) and extending away from the output rotational axis A0. In this manner, guide wire capability can be also provided to the multi-mode torque driver 108(3) with a relatively small size of the center portion 140(3) to minimize obstructions to other medical devices needing access to the vertebra 102A during surgery.

Figure 7C:
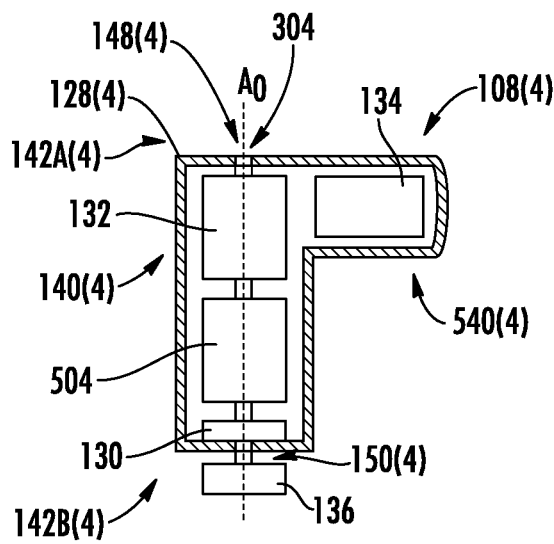

Next, FIG. 7C illustrates a front sectional view of a multi-mode torque driver 108(4). The main body 128(4) includes a center portion 140(4) extending along the output rotational axis A0 from a first end 142A(4) to a second end 142B(4). The main body 128(4) includes a cannulation port 148(4) at the first end 142A(4) and an output opening 150(4) at the second end 142B(4) and both disposed along the output rotational axis A0. The inner surface 144(4) of the main body 128(4) forms an inner space 146(4) connecting the cannulation port 148(4) and the output opening 150(4) and forming a passageway for the guide wire 106 along the output rotational axis A0. The anti-backdrive unit 130, motor 132, and drive train 504(4) may be disposed within the center portion 140(4) while the battery 134 is disposed in a protrusion 704(4) extending from the center portion 140(4) at the first end 142A(4) and extending away from the output rotational axis A0. The motor 132 needs to be provided with a pathway for the guide wire 106. In this manner, guide wire capability can be provided multi-mode torque driver 108(4) with a relatively small size of the protrusion 704(4) to minimize bulkiness in situations where the user 125 may have smaller hands.

Figure 7D:
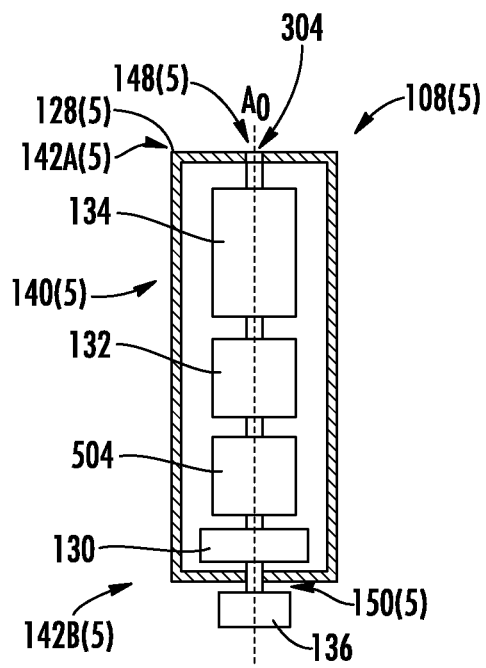

Next, FIG. 7D illustrates a front sectional view of a multi-mode torque driver 108(5). The main body 128(5) includes a center portion 140(5) extending along the output rotational axis A0 from a first end 142A(5) to a second end 142B(5). The main body 128(5) includes a cannulation port 148(5) at the first end 142A(5) and an output opening 150(5) at the second end 142B(5) and both disposed along the output rotational axis A0. The inner surface 144(5) of the main body 128(5) forms an inner space 146(5) connecting the cannulation port 148(5) and the output opening 150(5) and forming a passageway for the guide wire 106 along the output rotational axis A0. The anti-backdrive unit 130, motor 132, battery 134, and drive train 504(5) all may be disposed within the center portion 140(5). The motor 132 needs to be provided with a pathway for the guide wire 106. In this manner, guide wire capability can be provided to the multi-mode torque driver 108(5) free from a protrusion of the main body 128(5) to minimize size of the multi-mode torque driver 108(5) when working on patients with smaller than average-size vertebra 102A.

Other embodiments of the anti-backdrive unit are also possible. FIGS. 8A and 8B are partial top sectional views parallel to the output rotational axis of a second embodiment of a multi-mode torque driver 130X illustrating another embodiment of an anti-backdrive unit 108X operating in power mode 400A and manual mode 400B, respectively. The anti-backdrive unit 108X has some features similar to the anti-backdrive unit 108 and so mainly differences will be discussed in the interest of conciseness and clarity.

In this regard, similar to the anti-backdrive unit 108, the anti-backdrive unit 108X includes the output element 414, the at least one locking element 416(1)-416(N3), and the housing portion 520. The post portions 518(1)-518(N7) of the output interface 412 of the motor assembly 401, radial elements 517(1)-517(N6) and the at least one locking element 416(1)-416(N3) may be disposed within the housing portion 520 where they may be rotatable about the output rotational axis A0. During the power mode 400A, the motorized torque $T_{MOT}$ may rotate the post portions 518(1)-518(N7) of the output interface 412 within the housing portion 520. This rotation may cause the post portions 518(1)-518(N7) to abut against the at least one locking element 416(1)-416(N3) to move the at least one locking element 416(1)-416(N3) along the inner circumferential surface 522 of the housing portion 520. The rotation of the post portions 518(1)-518(N7) may also cause the post portions 518(1)-518(N7) to couple with the radial elements 517(1)-517(N6) of the output element 414 and transfer the motorized torque $T_{MOT}$ to the output element 414 as the system torque T0 which may rotate the pedicle screw 104A (FIG. 4A). The motorized torque $T_{MOT}$ may be received directly by the output element 414 from the post portions 518(1)-518(N7) as the two abut against each other. The output element 414 includes the inner surface 415 forming the passageway 417 through the output element 414 to facilitate the guide wire 106 to be inserted therethrough. In this manner, the pedicle screw 104A may be rotated during the power mode 400A while being precisely positioned along the guide wire 106 relative to the vertebra 102A.

In the manual mode 400B, the wherein upon a manual torque being applied to the main body 128 by a single hand of the user 125 while the output element 414 may be coupled to the pedicle screw 104A and the output element 414 may be free from the motorized torque $T_{MOT}$, then the manual torque $T_{MAN}$ moves the main body 128 relative to the output element 414 until the at least one locking element 416(1)-416(N3) abuts against both the inner circumferential surface 522 of the housing portion 520 and a non-concentric external surface 528 of the output element 414 to create a mechanical interference which automatically locks the output element 414 relative to the housing portion 520 statically coupled to the main body 128 and transmits the manual torque $T_{MAN}$ from the main body 128 to the output element 414 as the system torque T0 in the manual mode 400B. In this manner, the pedicle screw 104A may be rotated with the manual torque $T_{MAN}$ during the manual mode 400B while being precisely positioned along the guide wire 106 relative to the vertebra 102A.

Many modifications and other embodiments not set forth herein will come to mind to one skilled in the art to which the embodiments pertain having the benefit of the teachings presented in the foregoing descriptions and the associated drawings. Therefore, it is to be understood that the description and claims are not to be limited to the specific embodiments disclosed and that modifications and other embodiments are intended to be included within the scope of the appended claims. It is intended that the embodiments cover the modifications and variations of the embodiments provided they come within the scope of the appended claims and their equivalents. Although specific terms are employed herein, they are used in a generic and descriptive sense only and not for purposes of limitation.

What is claimed is:

1. A main body of a multi-mode torque driver for managing a pedicle screw attachment with a vertebra, the main body comprising:
    a center portion extending along an output rotational axis from a first end to a second end, wherein the center portion is arranged to transfer a manual torque from the first end to the second end; and
    an inner surface forming an inner space and the inner surface connecting a cannulation port at the first end to an output opening at the second end, wherein the inner surface includes a motor mounting interface configured to receive a motor coupled to the inner surface, wherein the output opening is configured for an output element of an anti-backdrive unit to extend through the output opening and convey a motorized torque from the motor during a power mode and the manual torque during a manual mode,
    wherein the output rotational axis extends through both the cannulation port and the output opening.

2. The main body of claim 1, wherein the cannulation port includes a width in a range from two (2) millimeters to three (3) millimeters.

3. The main body of claim 1, wherein the motor mounting interface is configured to couple with the motor so that the motorized torque generated by the motor is disposed at a transmission angle relative to the output rotational axis, wherein the transmission angle is in a range from forty-five degrees to ninety degrees.

4. A multi-mode torque driver for managing a pedicle screw attachment with a vertebra, comprising:
    a main body extending along an output rotational axis from a first end to a second end, the main body including an inner surface forming an inner space connecting a cannulation port at the first end to an output opening at the second end;
    a motor assembly disposed within the inner space; and
    an anti-backdrive unit coupled to the motor assembly, the anti-backdrive unit including an output element disposed through the output opening and along the output rotational axis, wherein the output element includes a first inner surface forming an output passageway through the output element and along the output rotational axis, and
    wherein the output element and the main body are configured to receive a guide wire along the output rotational axis and through the output passageway and the cannulation port while managing a pedicle screw attachment.

5. The multi-mode torque driver of claim 4, wherein the anti-backdrive unit further includes:
    at least one locking element, and
    a housing portion statically coupled to the inner surface of the main body at the second end of the main body and including an inner circumferential surface,
    wherein the anti-backdrive unit is disposed within the inner space,
    wherein the at least one locking element, the output element, and an output interface of the motor assembly are rotatable about the output rotational axis and disposed within the housing portion,
    wherein upon the output element of the anti-backdrive unit receiving a motorized torque from the motor assembly in a power mode as a system torque, the output element rotates and the output interface of the motor assembly abuts against the at least one locking element to move the at least one locking element along the inner circumferential surface, and
    wherein upon a manual torque being applied to the main body by a single hand of a user while the output element is coupled to a pedicle screw and the output element is free from the motorized torque, then the manual torque moves the main body relative to the output element until the at least one locking element abuts against both the inner circumferential surface of the housing portion and a non-concentric external surface of the output element to create a mechanical interference which automatically locks the output element relative to the main body and transmits the manual torque from the main body to the output element as the system torque in a manual mode.

6. The multi-mode torque driver of claim 4, wherein the guide wire has a width in a range from 1.5 millimeters to 2.0 millimeters.

7. The multi-mode torque driver of claim 4, wherein the motor assembly comprises a carrier backplane including a second inner surface forming a passageway for the guide wire along the output rotational axis and through the carrier backplane.

8. The multi-mode torque driver of claim 4, wherein the motor assembly includes a bevel gear with an axis of rotation disposed at a transmission angle relative to the output rotational axis, wherein the transmission angle is in a range from forty-five (45) degrees to ninety (90) degrees.

9. The multi-mode torque driver of claim 4, wherein the motor assembly includes at least one epicyclic gear train stage having a collective gear ratio in a range from 30:1 to 140:1.

10. The multi-mode torque driver of claim 4, wherein the motor assembly comprises an output interface including a third inner surface forming a passageway for the guide wire along the output rotational axis and through the output interface.

11. The multi-mode torque driver of claim 4, further comprising at least one switch disposed at one or more motor control ports of the main body, wherein the at least one switch comprises a plurality of non-zero speed positions.

12. The multi-mode torque driver of claim 11, wherein the at least one switch includes a rocker switch comprising the plurality of non-zero speed positions for a user to respectively select clockwise and counterclockwise directions of a motorized torque.

13. A method for managing a pedicle screw attachment with a vertebra, comprising:
    receiving a guide wire with a multi-mode torque driver, wherein the multi-mode torque driver includes a main body extending along an output rotational axis from a first end to a second end, the main body including an inner surface forming an inner space connecting a cannulation port at the first end to an output opening at the second end, wherein the guide wire is received by the main body and an output element of an anti-backdrive unit of the multi-mode torque driver, and wherein the guide wire is received along the output rotational axis and through an output passageway and the cannulation port, wherein the output element is disposed through the output opening and along the output rotational axis, wherein the output element includes a first inner surface forming the output passageway through the output element and along the output rotational axis;

transmitting, with the output element of the anti-backdrive unit disposed within the main body of the multi-mode torque driver, a system torque from the output element to a pedicle screw, wherein the system torque includes a manual torque during a manual mode and a motorized torque during a power mode, wherein the system torque moves the pedicle screw relative to a vertebra;

generating, with a motor assembly disposed within the inner space, the motorized torque during the power mode and transmitting the motorized torque to the anti-backdrive unit with the motor assembly in the power mode, wherein the anti-backdrive unit is coupled to the motor assembly; and upon applying the manual torque to the main body with a single hand of a user while the output element is coupled to the pedicle screw and the output element is free from the motorized torque, automatically locking the output element in the manual mode relative to the main body and transmitting the manual torque from the main body to the output element in the manual mode.

14. The method of claim 13, wherein the receiving includes the guide wire having a width in a range from 1.5 millimeters to 2.0 millimeters.

15. The method of claim 14, wherein the guide wire includes a Kirschner-type wire secured to a pedicle of the vertebra.

16. The method of claim 13, further comprising selecting a direction of the motorized torque, with at least one switch of the multi-mode torque driver, wherein the at least one switch comprises a plurality of non-zero speed positions corresponding to the direction of the motorized torque including a clockwise direction and a counterclockwise direction.

17. The method of claim 13, wherein the receiving further includes passing the guide wire along the output rotational axis and through a passageway of a carrier backplane of the motor assembly, wherein the carrier backplane includes a second inner surface forming the passageway.

18. The method of claim 13, wherein the transmitting the motorized torque to the anti-backdrive unit during the power mode includes transmitting the motorized torque through a bevel gear of the motor assembly, wherein the bevel gear has an axis of rotation disposed at a transmission angle relative to the output rotational axis, wherein the transmission angle is in a range from forty-five (45) degrees to ninety (90) degrees.

19. The method of claim 13, wherein the generating the motorized torque includes rotating about the output rotational axis: at least one locking element of the anti-backdrive unit, the output element, and an output interface of the motor assembly.

\* \* \* \* \*